US011261461B2

(12) United States Patent
Zheng et al.

(10) Patent No.: US 11,261,461 B2
(45) Date of Patent: Mar. 1, 2022

(54) METHODS AND COMPOSITIONS FOR SELECTIVE GENERATION OF DOPAMINERGIC PRECURSORS

(71) Applicants: TONGJI UNIVERSITY, Shanghai (CN); BOARD OF REGENTS OF THE UNIVERSITY OF NEBRASKA, Lincoln, NE (US)

(72) Inventors: Jialin Zheng, Omaha, NE (US); Changhai Tian, Omaha, NE (US)

(73) Assignees: Tongji University, Shanghai (CN); Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 15/503,649

(22) PCT Filed: Aug. 19, 2015

(86) PCT No.: PCT/CN2015/087503
§ 371 (c)(1),
(2) Date: Feb. 13, 2017

(87) PCT Pub. No.: WO2016/026438
PCT Pub. Date: Feb. 25, 2016

(65) Prior Publication Data
US 2017/0268021 A1 Sep. 21, 2017

Related U.S. Application Data

(60) Provisional application No. 62/038,914, filed on Aug. 19, 2014.

(51) Int. Cl.

| | |
|---|---|
| ***C12N 5/06*** | (2006.01) |
| ***C12N 15/86*** | (2006.01) |
| ***C12N 5/0793*** | (2010.01) |
| ***A61K 35/12*** | (2015.01) |

(52) U.S. Cl.
CPC .............. *C12N 15/86* (2013.01); *A61K 35/12* (2013.01); *C12N 5/0619* (2013.01); *C12N 2501/60* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 8,962,314 B2 * | 2/2015 | Yamoah ............... | C12N 5/0623 435/325 |
| 2003/0082812 A1 | 5/2003 | Goldman et al. | |

FOREIGN PATENT DOCUMENTS

| | | |
|---|---|---|
| CN | 101027390 A | 8/2007 |
| CN | 101466836 A | 6/2009 |
| JP | 2014516528 A | 7/2014 |

OTHER PUBLICATIONS

Wilson et al Scientific Discovery and the Future of Medicine JAMA Apr. 28, 2015 pp. 1613-1614.*
Sheng et al., Direct Conversion of Mouse Somatic Cells into Multipotent Neural Stem/Progenitor Cells and Mature Dopaminergic Neurons by Defied Factors. Chinese Doctoral Dissertations Fuii-text Database Med and Health Sci, 15 Mar. 2013 pp. 1-72.*
Tian et al Selective Generation of Dopaminergic Precursors from Mouse Fibroblasts by Direct Lineage Conversion 2015; Scientific Reports | pp. 1-14.*
Sheng Chao Direct Conversion of Mouse Somatic Cells Into Multipotent Neural Stem/Progenitor Cells and Mature Dopaminergic ; Dissertation for the Doctoral Degree in Science; Date of Oral Examination Jun. 2012; pp. 1-72.*
Ma et al., Doctoral Thesis Dissertation, Apr. 2013; Direct Convesion of Astrocytes into Telencephalic Neuronal Progenitor Cell-like Cells with Defined Transcription Factors, pp. 1-12 UMI No. 3571823.*
Mayshar et al., dentification and Classification of Chromosomal Aberrations in Human Induced Pluripotent Stem Cells; Cell Stem Cell 7, 521-531, Oct. 8, 2010.*
Sheng, Chao. Direct Conversion of Mouse Somatic Cells into Multipotent Neural Stem/Progenitor Cells and Mature Dopaminergic Neurons by Defined Factors. Chinese Doctoral Dissertations Full-text Database Med and Health Sci, Mar. 15, 2013.

* cited by examiner

*Primary Examiner* — Maria G Leavitt
(74) *Attorney, Agent, or Firm* — Weisun Rao; Sunyong Trang; Venture Partner, LLC

(57) ABSTRACT

Provided are methods and compositions for transdifferentiation of a somatic cell, e.g., a fibroblast to a dopaminergic precursor, Specifically, provided are induced dopaminergic (iDP) cells, or master transcription factors (TFs) therefore, methods for making iDP cells, and methods and compositions for using them in, e.g., treating neurodegenerative diseases such as Parkinson's disease.

11 Claims, 12 Drawing Sheets

Specification includes a Sequence Listing.

SEQUENCE LISTING

<160> NUMBER OF SEQ ID NOS: 74

<210> SEQ ID NO 1
<211> LENGTH: 1338
<212> TYPE: DNA
<213> ORGANISM: Mus musculus

<400> SEQUENCE: 1

```
atggcgaccg cagcgtctaa ccactacagc ctgctcacct ccagcgcctc catcgtacat     60

gccgagccgc ctggcggcat gcagcagggc gcagggggct accgcgaggc gcagagcctg    120

gtgcagggcg actacggcgc gctgcagagc aacgggcacc cgctcagcca cgctcaccag    180

tggatcaccg cgctgtccca cggcggcggc ggcgggggcg gcggcggcgg tggaggaggc    240

gggggaggcg gcgggggagg cggcgacggc tccccgtggt ccaccagccc cctaggccag    300

ccggacatca agccctcggt ggtggtacag cagggtggcc gaggcgacga gctgcacggg    360

ccaggagcgc tgcagcaaca gcatcaacag caacagcaac agcagcagca gcagcagcag    420

cagcagcagc agcaacagca gcagcaacaa cagcgaccgc cacatctggt gcaccacgct    480

gccaaccacc atcccgggcc cggggcatgg cggagtgcgg cggctgcagc tcacctccct    540

ccctccatgg gagcttccaa cggcggtttg ctctattcgc agccgagctt cacggtgaac    600

ggcatgctgg gcgcaggagg gcagccggct gggctgcacc accacggcct gagggacgcc    660

cacgatgagc cacaccatgc agaccaccac ccgcatccgc actctcaccc acaccagcaa    720

ccgcccccgc cacctccccc acaaggccca ccgggccacc caggcgcgca ccacgacccg    780

cactcggacg aggacacgcc gacctcagac gacctggagc agttcgccaa gcaattcaag    840

cagaggcgga tcaaactcgg atttactcaa gcagacgtgg ggctggcgct tggcaccctg    900

tacggcaacg tgttctcgca gaccaccatc tgcaggtttg aggccctgca gctgagcttc    960

aagaacatgt gcaagctgaa gcctttgttg aacaagtggt tggaagaggc agactcatcc   1020

tcgggcagcc ccaccagcat agacaagatc gcagcgcaag ggcgcaaacg gaaaaagcgg   1080

acctccatcg aggtgagcgt caagggggct ctggagagcc atttcctcaa atgccctaag   1140

ccctcggccc aggagatcac ctccctcgcg gacagcttac agctggagaa ggaggtggtg   1200

agagtttggt tttgtaacag gagacagaaa gagaaaagga tgacccctcc cggaggggact   1260

ctgccgggcg ccgaggatgt gtatgggggt agtagggaca cgccaccaca ccacggggtg   1320

cagacgcccg tccagtga                                                 1338
```

<210> SEQ ID NO 2
<211> LENGTH: 1086
<212> TYPE: DNA
<213> ORGANISM: Mus musculus

<400> SEQUENCE: 2

```
atggccacag ctgcctcgaa tccctacagc attctcagtt ccagctccct tgtccatgcg     60

gactccgcgg gcatgcagca gggaagtcct ttccgcaatc ctcagaaact tctccaaagt    120

gactacttgc agggagttcc cagcaatggg catcccctcg ggcatcactg ggtgaccagt    180

cttagcgacg gggcccgtg gtcctccaca ttggccacca gccccctgga ccagcaagac    240

gtgaagccgg gacgcgaaga tctgcaactg ggcgcaatca tccatcaccg ctcgccgcac    300

gtagcccacc actcgccgca cactaaccat ccgaacgcct ggggagcgag ccctgctcca    360

aactcgtcca tcacgtccag cggccaaccc ctcaatgtgt actcgcagcc aggcttcacc    420

gtgagcggta tgctggagca cgggggactc actccaccac cagctgctgc ctccacacag    480
```

agcctgcatc cagtgctccg ggagcctcca gaccatggtg agctgggctc gcaccactgc 540
caggaccact ctgatgaaga gactccaacc tctgatgagt tggaacagtt cgccaaacaa 600
ttcaaacaaa gaagaatcaa gttgggcttc acgcaagccg acgtggggct ggcactgggc 660
acactgtatg gcaacgtgtt ctcgcagact accatctgca ggttcgaggc cttacaactg 720
agcttcaaga acatgtgcaa gctgaaaccg ctattaaata agtggctgga ggaggctgat 780
tcatccacag gaagcccgac cagcattgac aagatcgctg ctcaaggccg caaacgcaag 840
aagcgaacct ccatcgaggt gagtgtcaag ggcgtactgg aaacacattt cctcaagtgt 900
cccaagcctg cagcgcagga gatctcctcg ctggcagaca gtctccagtt ggagaaagaa 960
gtggtgcgtg tctggttctg taatagaaga caaaaagaaa aaagaatgac tccgccaggg 1020
gatcagcagc cacacgaggt ttattcgcac acggtgaaaa cagacgcgtc ctgccacgat 1080
ctctga 1086

<210> SEQ ID NO 3
<211> LENGTH: 969
<212> TYPE: DNA
<213> ORGANISM: Mus musculus

<400> SEQUENCE: 3
atgtataaca tgatggagac ggagctgaag ccgccgggcc cgcagcaagc ttcggggggc 60
ggcggcggag gaggcaacgc cacggcggcg gcgaccggcg gcaaccagaa gaacagcccg 120
gaccgcgtca agaggcccat gaacgccttc atggtatggt cccgggggca gcggcgtaag 180
atggcccagg agaaccccaa gatgcacaac tcggagatca gcaagcgcct gggcgcggag 240
tggaaacttt tgtccgagac cgagaagcgg ccgttcatcg acgaggccaa gcggctgcgc 300
gctctgcaca tgaaggagca cccggattat aaataccggc cgcggcggaa aaccaagacg 360
ctcatgaaga aggataagta cacgcttccc ggaggcttgc tggcccccgg cgggaacagc 420
atggcgagcg gggttggggt gggcgccggc ctgggtgcgg gcgtgaacca gcgcatggac 480
agctacgcgc acatgaacgg ctggagcaac ggcagctaca gcatgatgca ggagcagctg 540
ggctacccgc agcacccggg cctcaacgct cacggcgcgg cacagatgca accgatgcac 600
cgctacgacg tcagcgccct gcagtacaac tccatgacca gctcgcagac ctacatgaac 660
ggctcgccca cctacagcat gtcctactcg cagcagggca cccccggtat ggcgctgggc 720
tccatgggct ctgtggtcaa gtccgaggcc agctccagcc cccccgtggt tacctcttcc 780
tcccactcca gggcgccctg ccaggccggg gacctccggg acatgatcag catgtacctc 840
cccggcgccg aggtgccgga gcccgctgcg cccagtagac tgcacatggc ccagcactac 900
cagagcggcc cggtgcccgg cacggccatt aacggcacac tgcccctgtc gcacatgtga 960
gggctggac 969

<210> SEQ ID NO 4
<211> LENGTH: 1398
<212> TYPE: DNA
<213> ORGANISM: Mus musculus

<400> SEQUENCE: 4
atgcactcgg cttccagtat gctgggagcc gtgaagatgg aagggcacga gccatccgac 60
tggagcagct actacgcgga gcccgagggc tactcttccg tgagcaacat gaacgccggc 120
ctggggatga atggcatgaa cacatacatg agcatgtccg cggctgccat gggcggcggt 180

```
tccggcaaca tgagcgcggg ctccatgaac atgtcatcct atgtgggcgc tggaatgagc    240

ccgtcgctag ctggcatgtc cccgggcgcc ggcgccatgg cgggcatgag cggctcagcc    300

ggggcggccg gcgtggcggg catgggacct cacctgagtc cgagtctgag cccgctcggg    360

ggacaggcgg ccggggccat gggtggcctt gccccctacg ccaacatgaa ctcgatgagc    420

cccatgtacg ggcaggccgg cctgagccgc gctcgggacc ccaagacata ccgacgcagc    480

tacacacacg ccaaacctcc ctactcgtac atctcgctca tcaccatggc catccagcag    540

agccccaaca agatgctgac gctgagcgag atctatcagt ggatcatgga cctcttccct    600

ttctaccggc agaaccagca gcgctggcag aactccatcc gccactctct ctccttcaac    660

gactgctttc tcaaggtgcc ccgctcgcca gacaagcctg gcaagggctc cttctggacc    720

ctgcacccag actcgggcaa catgttcgag aacggctgct acctgcgccg ccagaagcgc    780

ttcaagtgtg agaagcaact ggcactgaag gaagccgcgg gtgcggccag tagcggaggc    840

aagaagaccg ctcctgggtc ccaggcctct caggctcagc tcggggaggc cgcgggctcg    900

gcctccgaga ctccggcggg caccgagtcc ccccattcca gcgcttctcc gtgtcaggag    960

cacaagcgag gtggcctaag cgagctaaag ggagcacctg cctctgcgct gagtcctccc   1020

gagccggcgc cctcgcctgg gcagcagcag caggctgcag cccacctgct gggcccacct   1080

caccacccag gcctgccacc agaggcccac ctgaagcccg agcaccatta cgccttcaac   1140

caccccttct ctatcaacaa cctcatgtcg tccgagcagc aacatcacca cagccaccac   1200

caccatcagc cccacaaaat ggacctcaag gcctacgaac aggtcatgca ctacccaggg   1260

ggctatggtt cccccatgcc aggcagcttg gccatgggcc cagtcacgaa caaagcgggc   1320

ctggatgcct cgcccctggc tgcagacact tcctactacc aaggagtgta ctccaggcct   1380

attatgaact catcctaa                                                 1398
```

<210> SEQ ID NO 5
<211> LENGTH: 1153
<212> TYPE: DNA
<213> ORGANISM: Mus musculus

<400> SEQUENCE: 5

```
atgttggacg gcctgaagat ggaggagaac tttcaaagtg cgattgagac ctcggcatct     60

ttctcctctt tgctgggcag agcggtgagc cccaagtctg tctgcgaggg ctgtcagcgg    120

gtcatctcgg acaggtttct gctgcggctc aacgacagct tctggcacga gcaatgcgtg    180

cagtgtgcct cctgcaaaga gcccctggag accacctgct tctaccggga caagaagctc    240

tactgcaagt accactacga gaaactgttt gctgtcaaat gtgggggctg cttcgaggcc    300

attgcgccca atgagtttgt catgcgtgcc cagaagagcg tataccacct gagctgcttc    360

tgctgctgcg tctgtgagcg acagctgcag aagggtgacg agtttgtcct gaaggagggc    420

cagctgctct gcaaagggga ctatgagaaa gaacgggagc tgctgagcct ggtgagccct    480

gcggcctcag actcaggcaa aagcgatgat gaggagagcc tttgcaagtc agcccatggg    540

gcaggaaaag gagcatcaga ggacggcaag gaccataagc gacccaaacg tcccagaacc    600

atcctgacca ctcagcagag gagagcattc aaggcctcgt ttgaagtatc ctccaagccc    660

tgcagaaagg tgagggagac tctggctgcg gagacagggc tgagtgtccg tgtggttcag    720

gtgtggttcc agaaccagcg agccaagatg aagaagctgg cccggcgaca gcagcaacag    780

caacaggacc aacagaacac ccagaggctg acttctgctc agacaaatgg tagtgggaat    840

gcgggcatgg aagggatcat gaacccctat acaacgttgc ccaccccaca gcagctgctg    900
```

gccattgaac agagcgtcta caactctgat cccttccgac agggtctcac cccaccccag 960
atgcctggag atcacatgca cccctatggt gctgaacctc ttttccatga cttggatagt 1020
gatgacacat ctctcagtaa cctgggagac tgcttcctgg caacctcaga agctgggccc 1080
ctgcagtcca gagtgggaaa ccccattgac catctgtact ccatgcagaa ttcctatttc 1140
acctcttgag tct 1153

<210> SEQ ID NO 6
<211> LENGTH: 1332
<212> TYPE: DNA
<213> ORGANISM: Homo sapiens

<400> SEQUENCE: 6
atggcgaccg cagcgtctaa ccactacagc ctgctcacct ccagcgcctc catcgtgcac 60
gccgagccgc ccggcggcat gcagcagggc gcggggggct accgcgaagc gcagagcctg 120
gtgcagggcg actacggcgc tctgcagagc aacggacacc cgctcagcca cgctcaccag 180
tggatcaccg cgctgtccca cggcggcggc ggcgggggcg gtggcggcgg cggggggggc 240
gggggcggcg gcgggggcgg cggcgacggc tccccgtggt ccaccagccc cctgggccag 300
ccggacatca agccctcggt ggtggtgcag cagggcggcc gcggagacga gctgcacggg 360
ccaggcgccc tgcagcagca gcatcagcag cagcaacagc aacagcagca gcaacagcag 420
caacagcagc agcagcagca gcaacagcgg ccgccgcatc tggtgcacca cgccgctaac 480
caccacccgg gacccggggc atggcggagc gcggcggctg cagcgcacct cccaccctcc 540
atgggagcgt ccaacggcgg cttgctctac tcgcagccca gcttcacggt gaacggcatg 600
ctgggcgccg gcgggcagcc ggccggtctg caccaccacg gcctgcggga cgcgcacgac 660
gagccacacc atgccgacca ccacccgcac ccgcactcgc acccacacca gcagccgccg 720
cccccgccgc ccccgcaggg tccgcctggc cacccaggcg cgcaccacga cccgcactcg 780
gacgaggaca cgccgacctc ggacgacctg gagcagttcg ccaagcagtt caagcagcgg 840
cggatcaaac tgggatttac ccaagcggac gtggggctgg ctctgggcac cctgtatggc 900
aacgtgttct cgcagaccac catctgcagg tttgaggccc tgcagctgag cttcaagaac 960
atgtgcaagc tgaagccttt gttgaacaag tggttggagg aggcggactc gtcctcgggc 1020
agccccacga gcatagacaa gatcgcagcg caagggcgca agcggaaaaa gcggacctcc 1080
atcgaggtga gcgtcaaggg ggctctggag agccatttcc tcaaatgccc caagccctcg 1140
gcccaggaga tcacctccct cgcggacagc ttacagctgg agaaggaggt ggtgagagtt 1200
tggttttgta acaggagaca gaaagagaaa aggatgaccc ctcccggagg gactctgccg 1260
ggcgccgagg atgtgtacgg ggggagtagg gacactccac cacaccacgg ggtgcagacg 1320
cccgtccagt ga 1332

<210> SEQ ID NO 7
<211> LENGTH: 1086
<212> TYPE: DNA
<213> ORGANISM: Homo sapiens

<400> SEQUENCE: 7
atggccacag ctgcctcgaa tccctacagc attctcagtt ccacctccct agtccatgcg 60
gactctgcgg gcatgcagca ggggagtcct ttccgcaacc ctcagaaact tctccaaagt 120
gattacttgc agggagttcc cagcaatggg catcccctcg ggcatcactg ggtgaccagt 180

```
ctgagcgacg ggggcccatg gtcctccaca ctggccacca gccccctgga ccagcaggac    240

gtgaagcccg ggcgcgaaga cctgcaactg ggtgcgatca tccatcaccg ctcgccacac    300

gtagcccacc actcaccgca cactaaccac cccaacgcct ggggggccag cccggcaccg    360

aacccgtcta tcacgtcaag cggccaaccc ctcaacgtgt actcgcagcc tggcttcacc    420

gtgagcggca tgctggaaca cgggggactc accccacctc cagctgccgc ctctgcacag    480

agcctgcacc cggtgctccg agagcccccg gatcacggcg aactgggctc gcaccattgc    540

caggatcact ccgacgagga gacgccaacc tctgatgagt tggaacagtt cgccaaacaa    600

ttcaaacaaa gaagaatcaa gttgggcttc acgcaggccg acgtggggtt ggcgctgggc    660

acactgtatg gtaacgtgtt ctcgcagacc accatctgca ggttcgaggc cttgcagctg    720

agcttcaaaa atatgtgcaa gctgaagccc ctgctgaaca agtggctgga ggaggcggat    780

tcgtccacag ggagcccgac cagcattgac aagatcgctg cacagggccg caagcgcaag    840

aagcggacct ccatcgaggt gagtgtcaag ggcgtactgg agacgcattt cctcaagtgt    900

cccaagcctg ccgcgcagga gatctcctcg ctggcagaca gcctccagtt ggagaaggaa    960

gtggtgcgtg tctggttctg taatcgaaga caaaaagaga aaagaatgac tccgccaggg   1020

gatcagcagc cgcatgaggt ttattcgcac accgtgaaaa cagacacatc ttgccatgat   1080

ctctga                                                              1086
```

<210> SEQ ID NO 8
<211> LENGTH: 954
<212> TYPE: DNA
<213> ORGANISM: Homo sapiens

<400> SEQUENCE: 8

```
atgtacaaca tgatggagac ggagctgaag ccgccgggcc cgcagcaaac ttcggggggc     60

ggcggcggca actccaccgc ggcggcggcc ggcggcaacc agaaaaacag cccggaccgc    120

gtcaagcggc ccatgaatgc cttcatggtg tggtcccgcg ggcagcggcg caagatggcc    180

caggagaacc ccaagatgca caactcggag atcagcaagc gcctgggcgc cgagtggaaa    240

cttttgtcgg agacggagaa gcggccgttc atcgacgagg ctaagcggct gcgagcgctg    300

cacatgaagg agcacccgga ttataaatac cggccccggc ggaaaaccaa gacgctcatg    360

aagaaggata agtacacgct gcccggcggg ctgctggccc ccggcggcaa tagcatggcg    420

agcggggtcg gggtgggcgc cggcctgggc gcgggcgtga accagcgcat ggacagttac    480

gcgcacatga acggctggag caacggcagc tacagcatga tgcaggacca gctgggctac    540

ccgcagcacc cgggcctcaa tgcgcacggc gcagcgcaga tgcagcccat gcaccgctac    600

gacgtgagcg ccctgcagta caactccatg accagctcgc agacctacat gaacggctcg    660

cccacctaca gcatgtccta ctcgcagcag ggcacccctg gcatggctct tggctccatg    720

ggttcggtgg tcaagtccga ggccagctcc agcccccctg tggttacctc ttcctcccac    780

tccagggcgc cctgccaggc cggggacctc cgggacatga tcagcatgta tctccccggc    840

gccgaggtgc cggaacccgc cgcccccagc agacttcaca tgtcccagca ctaccagagc    900

ggcccggtgc ccggcacggc cattaacggc acactgcccc tctcacacat gtga          954
```

<210> SEQ ID NO 9
<211> LENGTH: 1392
<212> TYPE: DNA
<213> ORGANISM: Homo sapiens

<400> SEQUENCE: 9
atgcactcgg cttccagtat gctgggagcg gtgaagatgg aagggcacga gccgtccgac 60
tggagcagct actatgcaga gcccgagggc tactcctccg tgagcaacat gaacgccggc 120
ctggggatga acggcatgaa cacgtacatg agcatgtcgg cggccgccat gggcagcggc 180
tcgggcaaca tgagcgcggg ctccatgaac atgtcgtcgt acgtgggcgc tggcatgagc 240
ccgtccctgg cggggatgtc ccccggcgcg ggcgccatgg cgggcatggg cggctcggcc 300
ggggcggccg gcgtggcggg catggggccg cacttgagtc ccagcctgag cccgctcggg 360
gggcaggcgg ccggggccat gggcggcctg gccccctacg ccaacatgaa ctccatgagc 420
cccatgtacg ggcaggcggg cctgagccgc gcccgcgacc ccaagaccta caggcgcagc 480
tacacgcacg caaagccgcc ctactcgtac atctcgctca tcaccatggc catccagcag 540
agccccaaca agatgctgac gctgagcgag atctaccagt ggatcatgga cctcttcccc 600
ttctaccggc agaaccagca gcgctggcag aactccatcc gccactcgct ctccttcaac 660
gactgtttcc tgaaggtgcc ccgctcgccc gacaagcccg gcaagggctc cttctggacc 720
ctgcaccctg actcgggcaa catgttcgag aacggctgct acctgcgccg ccagaagcgc 780
ttcaagtgcg agaagcagct ggcgctgaag gaggccgcag gcgccgccgg cagcggcaag 840
aaggcggccg ccggagccca ggcctcacag gctcaactcg gggaggccgc cgggccggcc 900
tccgagactc cggcgggcac cgagtcgcct cactcgagcg cctccccgtg ccaggagcac 960
aagcgagggg gcctgggaga gctgaagggg acgccggctg cggcgctgag ccccccagag 1020
ccggcgccct ctcccgggca gcagcagcag gccgcggccc acctgctggg cccgccccac 1080
cacccgggcc tgccgcctga ggcccacctg aagccggaac accactacgc cttcaaccac 1140
ccgttctcca tcaacaacct catgtcctcg gagcagcagc accaccacag ccaccaccac 1200
caccagcccc acaaaatgga cctcaaggcc tacgaacagg tgatgcacta ccccggctac 1260
ggttccccca tgcctggcag cttggccatg ggcccggtca cgaacaaaac gggcctggac 1320
gcctcgcccc tggccgcaga tacctcctac taccaggggg tgtactcccg gcccattatg 1380
aactcctctt aa 1392

<210> SEQ ID NO 10
<211> LENGTH: 402
<212> TYPE: DNA
<213> ORGANISM: Homo sapiens

<400> SEQUENCE: 10
atgaagaagc tggccaggcg acagcagcag cagcagcaag atcagcagaa cacccagagg 60
ctgagctctg ctcagacaaa cggtggtggg agtgctggga tggaaggaat catgaacccc 120
tacacggctc tgcccacccc acagcagctc ctggccatcg agcagagtgt ctacagctca 180
gatcccttcc gacagggtct caccccaccc cagatgcctg gagaccacat gcacccttat 240
ggtgccgagc cccttttcca tgacctggat agcgacgaca cctccctcag taacctgggt 300
gactgtttcc tagcaacctc agaagctggg cctctgcagt ccagagtggg aaaccccatt 360
gaccatctgt actccatgca gaattcttac ttcacatctt ga 402

<210> SEQ ID NO 11
<211> LENGTH: 20
<212> TYPE: DNA
<213> ORGANISM: Unknown
<220> FEATURE:
<223> OTHER INFORMATION: Synthetic

<400> SEQUENCE: 11
gagtgtgacg tgcttccaga 20

<210> SEQ ID NO 12
<211> LENGTH: 20
<212> TYPE: DNA
<213> ORGANISM: Unknown
<220> FEATURE:
<223> OTHER INFORMATION: Synthetic

<400> SEQUENCE: 12
tggtcccagt tgatcatggc 20

<210> SEQ ID NO 13
<211> LENGTH: 19
<212> TYPE: DNA
<213> ORGANISM: Unknown
<220> FEATURE:
<223> OTHER INFORMATION: Synthetic

<400> SEQUENCE: 13
tgcgctgtcg ttatcggac 19

<210> SEQ ID NO 14
<211> LENGTH: 21
<212> TYPE: DNA
<213> ORGANISM: Unknown
<220> FEATURE:
<223> OTHER INFORMATION: Synthetic

<400> SEQUENCE: 14
ggtagcgatt cctctggaag g 21

<210> SEQ ID NO 15
<211> LENGTH: 19
<212> TYPE: DNA
<213> ORGANISM: Unknown
<220> FEATURE:
<223> OTHER INFORMATION: Synthetic

<400> SEQUENCE: 15
acggcctgaa gatggagga 19

<210> SEQ ID NO 16
<211> LENGTH: 21
<212> TYPE: DNA
<213> ORGANISM: Unknown
<220> FEATURE:
<223> OTHER INFORMATION: Synthetic

<400> SEQUENCE: 16
cagaaacctg tccgagatga c 21

<210> SEQ ID NO 17
<211> LENGTH: 21
<212> TYPE: DNA
<213> ORGANISM: Unknown
<220> FEATURE:
<223> OTHER INFORMATION: Synthetic

<400> SEQUENCE: 17
ctgcacagta tggccgagat g 21

<210> SEQ ID NO 18
<211> LENGTH: 19

<212> TYPE: DNA
<213> ORGANISM: Unknown
<220> FEATURE:
<223> OTHER INFORMATION: Synthetic

<400> SEQUENCE: 18
ccgggttatg tgagcccaa 19

<210> SEQ ID NO 19
<211> LENGTH: 21
<212> TYPE: DNA
<213> ORGANISM: Unknown
<220> FEATURE:
<223> OTHER INFORMATION: Synthetic

<400> SEQUENCE: 19
tgctgctatg acttctttgc c 21

<210> SEQ ID NO 20
<211> LENGTH: 19
<212> TYPE: DNA
<213> ORGANISM: Unknown
<220> FEATURE:
<223> OTHER INFORMATION: Synthetic

<400> SEQUENCE: 20
gcttcctgtg atcggccat 19

<210> SEQ ID NO 21
<211> LENGTH: 21
<212> TYPE: DNA
<213> ORGANISM: Unknown
<220> FEATURE:
<223> OTHER INFORMATION: Synthetic

<400> SEQUENCE: 21
tggaggtgcc tatcagagag a 21

<210> SEQ ID NO 22
<211> LENGTH: 22
<212> TYPE: DNA
<213> ORGANISM: Unknown
<220> FEATURE:
<223> OTHER INFORMATION: Synthetic

<400> SEQUENCE: 22
gtgagatcca gtaacgcatt ca 22

<210> SEQ ID NO 23
<211> LENGTH: 19
<212> TYPE: DNA
<213> ORGANISM: Unknown
<220> FEATURE:
<223> OTHER INFORMATION: Synthetic

<400> SEQUENCE: 23
gcaaccgggt caagttggt 19

<210> SEQ ID NO 24
<211> LENGTH: 20
<212> TYPE: DNA
<213> ORGANISM: Unknown
<220> FEATURE:
<223> OTHER INFORMATION: Synthetic

<400> SEQUENCE: 24
gtcgttggag tagttggggg 20

<210> SEQ ID NO 25
<211> LENGTH: 20
<212> TYPE: DNA
<213> ORGANISM: Unknown
<220> FEATURE:
<223> OTHER INFORMATION: Synthetic

<400> SEQUENCE: 25
gacattcccg gacacacacc 20

<210> SEQ ID NO 26
<211> LENGTH: 20
<212> TYPE: DNA
<213> ORGANISM: Unknown
<220> FEATURE:
<223> OTHER INFORMATION: Synthetic

<400> SEQUENCE: 26
ctcctcgtcc tcctcctcgt 20

<210> SEQ ID NO 27
<211> LENGTH: 19
<212> TYPE: DNA
<213> ORGANISM: Unknown
<220> FEATURE:
<223> OTHER INFORMATION: Synthetic

<400> SEQUENCE: 27
caaggctgac gcacttgga 19

<210> SEQ ID NO 28
<211> LENGTH: 20
<212> TYPE: DNA
<213> ORGANISM: Unknown
<220> FEATURE:
<223> OTHER INFORMATION: Synthetic

<400> SEQUENCE: 28
cttgccgttc ttcttgtcgc 20

<210> SEQ ID NO 29
<211> LENGTH: 22
<212> TYPE: DNA
<213> ORGANISM: Unknown
<220> FEATURE:
<223> OTHER INFORMATION: Synthetic

<400> SEQUENCE: 29
tatctaaagc aaccgcctta cg 22

<210> SEQ ID NO 30
<211> LENGTH: 21
<212> TYPE: DNA
<213> ORGANISM: Unknown
<220> FEATURE:
<223> OTHER INFORMATION: Synthetic

<400> SEQUENCE: 30
aagtccatac ccgaagtggt c 21

<210> SEQ ID NO 31
<211> LENGTH: 22
<212> TYPE: DNA
<213> ORGANISM: Unknown

<220> FEATURE:
<223> OTHER INFORMATION: Synthetic

<400> SEQUENCE: 31
catcatcaag gactcctcac gg 22

<210> SEQ ID NO 32
<211> LENGTH: 19
<212> TYPE: DNA
<213> ORGANISM: Unknown
<220> FEATURE:
<223> OTHER INFORMATION: Synthetic

<400> SEQUENCE: 32
gacatcacca acggggacg 19

<210> SEQ ID NO 33
<211> LENGTH: 19
<212> TYPE: DNA
<213> ORGANISM: Unknown
<220> FEATURE:
<223> OTHER INFORMATION: Synthetic

<400> SEQUENCE: 33
atgaagcgcc aggctaagg 19

<210> SEQ ID NO 34
<211> LENGTH: 21
<212> TYPE: DNA
<213> ORGANISM: Unknown
<220> FEATURE:
<223> OTHER INFORMATION: Synthetic

<400> SEQUENCE: 34
ggtttgccgt ctttgactag g 21

<210> SEQ ID NO 35
<211> LENGTH: 25
<212> TYPE: DNA
<213> ORGANISM: Unknown
<220> FEATURE:
<223> OTHER INFORMATION: Synthetic

<400> SEQUENCE: 35
ctggaacagc aaaacaaggc gctgg 25

<210> SEQ ID NO 36
<211> LENGTH: 23
<212> TYPE: DNA
<213> ORGANISM: Unknown
<220> FEATURE:
<223> OTHER INFORMATION: Synthetic

<400> SEQUENCE: 36
tccagcctca ggttggtttc atc 23

<210> SEQ ID NO 37
<211> LENGTH: 21
<212> TYPE: DNA
<213> ORGANISM: Unknown
<220> FEATURE:
<223> OTHER INFORMATION: Synthetic

<400> SEQUENCE: 37
accaaaagca acggagaaga g 21

<210> SEQ ID NO 38
<211> LENGTH: 22
<212> TYPE: DNA
<213> ORGANISM: Unknown
<220> FEATURE:
<223> OTHER INFORMATION: Synthetic

<400> SEQUENCE: 38
ggcattccga aacaggtaac tc 22

<210> SEQ ID NO 39
<211> LENGTH: 19
<212> TYPE: DNA
<213> ORGANISM: Unknown
<220> FEATURE:
<223> OTHER INFORMATION: Synthetic

<400> SEQUENCE: 39
ccctgaagtc gaggagctg 19

<210> SEQ ID NO 40
<211> LENGTH: 19
<212> TYPE: DNA
<213> ORGANISM: Unknown
<220> FEATURE:
<223> OTHER INFORMATION: Synthetic

<400> SEQUENCE: 40
ctgctgcacc tctaagcga 19

<210> SEQ ID NO 41
<211> LENGTH: 20
<212> TYPE: DNA
<213> ORGANISM: Unknown
<220> FEATURE:
<223> OTHER INFORMATION: Synthetic

<400> SEQUENCE: 41
tcttccaccg catcccttct 20

<210> SEQ ID NO 42
<211> LENGTH: 23
<212> TYPE: DNA
<213> ORGANISM: Unknown
<220> FEATURE:
<223> OTHER INFORMATION: Synthetic

<400> SEQUENCE: 42
ccgagtaggg taggataact tcg 23

<210> SEQ ID NO 43
<211> LENGTH: 21
<212> TYPE: DNA
<213> ORGANISM: Unknown
<220> FEATURE:
<223> OTHER INFORMATION: Synthetic

<400> SEQUENCE: 43
tccccagaac ccgatgatct t 21

<210> SEQ ID NO 44
<211> LENGTH: 19
<212> TYPE: DNA
<213> ORGANISM: Unknown
<220> FEATURE:
<223> OTHER INFORMATION: Synthetic

<400> SEQUENCE: 44
cgtggacgag gacacagtc 19

<210> SEQ ID NO 45
<211> LENGTH: 21
<212> TYPE: DNA
<213> ORGANISM: Unknown
<220> FEATURE:
<223> OTHER INFORMATION: Synthetic

<400> SEQUENCE: 45
aggggttcag cttttcggat t 21

<210> SEQ ID NO 46
<211> LENGTH: 23
<212> TYPE: DNA
<213> ORGANISM: Unknown
<220> FEATURE:
<223> OTHER INFORMATION: Synthetic

<400> SEQUENCE: 46
agtgttatca ttctccgggg tag 23

<210> SEQ ID NO 47
<211> LENGTH: 21
<212> TYPE: DNA
<213> ORGANISM: Unknown
<220> FEATURE:
<223> OTHER INFORMATION: Synthetic

<400> SEQUENCE: 47
tggttgccct cattgatgtc t 21

<210> SEQ ID NO 48
<211> LENGTH: 19
<212> TYPE: DNA
<213> ORGANISM: Unknown
<220> FEATURE:
<223> OTHER INFORMATION: Synthetic

<400> SEQUENCE: 48
cccatcccca tcttcgtcc 19

<210> SEQ ID NO 49
<211> LENGTH: 23
<212> TYPE: DNA
<213> ORGANISM: Unknown
<220> FEATURE:
<223> OTHER INFORMATION: Synthetic

<400> SEQUENCE: 49
gagatgatca gcatgtacct gcc 23

<210> SEQ ID NO 50
<211> LENGTH: 20
<212> TYPE: DNA
<213> ORGANISM: Unknown
<220> FEATURE:
<223> OTHER INFORMATION: synthetic

<400> SEQUENCE: 50
gtagtgctgt ggcagcgagt 20

<210> SEQ ID NO 51

<211> LENGTH: 20
<212> TYPE: DNA
<213> ORGANISM: Unknown
<220> FEATURE:
<223> OTHER INFORMATION: synthetic

<400> SEQUENCE: 51
tggcaaacaa cctgcctatg 20

<210> SEQ ID NO 52
<211> LENGTH: 21
<212> TYPE: DNA
<213> ORGANISM: Unknown
<220> FEATURE:
<223> OTHER INFORMATION: Synthetic

<400> SEQUENCE: 52
tgcacgagta tgaggaggtc t 21

<210> SEQ ID NO 53
<211> LENGTH: 20
<212> TYPE: DNA
<213> ORGANISM: Unknown
<220> FEATURE:
<223> OTHER INFORMATION: synthetic

<400> SEQUENCE: 53
tgttgttggc gcaaatgtgg 20

<210> SEQ ID NO 54
<211> LENGTH: 21
<212> TYPE: DNA
<213> ORGANISM: Unknown
<220> FEATURE:
<223> OTHER INFORMATION: synthetic

<400> SEQUENCE: 54
tgttccttga gcagataggg a 21

<210> SEQ ID NO 55
<211> LENGTH: 20
<212> TYPE: DNA
<213> ORGANISM: Unknown
<220> FEATURE:
<223> OTHER INFORMATION: Synthetic

<400> SEQUENCE: 55
cagctcgaga gaacgcatca 20

<210> SEQ ID NO 56
<211> LENGTH: 20
<212> TYPE: DNA
<213> ORGANISM: Unknown
<220> FEATURE:
<223> OTHER INFORMATION: Synthetic

<400> SEQUENCE: 56
acggggttct tgagttcagt 20

<210> SEQ ID NO 57
<211> LENGTH: 20
<212> TYPE: DNA
<213> ORGANISM: Unknown
<220> FEATURE:
<223> OTHER INFORMATION: synthetic

<400> SEQUENCE: 57
ctgggacttt gtgcgatgtg 20

<210> SEQ ID NO 58
<211> LENGTH: 22
<212> TYPE: DNA
<213> ORGANISM: Unknown
<220> FEATURE:
<223> OTHER INFORMATION: synthetic

<400> SEQUENCE: 58
cggtggaaga ggatctcaaa ca 22

<210> SEQ ID NO 59
<211> LENGTH: 21
<212> TYPE: DNA
<213> ORGANISM: Unknown
<220> FEATURE:
<223> OTHER INFORMATION: synthetic

<400> SEQUENCE: 59
ttctacgact atgactgcgg a 21

<210> SEQ ID NO 60
<211> LENGTH: 22
<212> TYPE: DNA
<213> ORGANISM: Unknown
<220> FEATURE:
<223> OTHER INFORMATION: synthetic

<400> SEQUENCE: 60
tgatggaagc ataattcctg cc 22

<210> SEQ ID NO 61
<211> LENGTH: 24
<212> TYPE: DNA
<213> ORGANISM: Unknown
<220> FEATURE:
<223> OTHER INFORMATION: synthetic

<400> SEQUENCE: 61
agctggagaa ggaggtggtg agag 24

<210> SEQ ID NO 62
<211> LENGTH: 31
<212> TYPE: DNA
<213> ORGANISM: Unknown
<220> FEATURE:
<223> OTHER INFORMATION: synthetic

<400> SEQUENCE: 62
cacctgctac ctgatatagg atagtccagt g 31

<210> SEQ ID NO 63
<211> LENGTH: 24
<212> TYPE: DNA
<213> ORGANISM: Unknown
<220> FEATURE:
<223> OTHER INFORMATION: synthetic

<400> SEQUENCE: 63
agctggagaa ggaggtggtg agag 24

<210> SEQ ID NO 64
<211> LENGTH: 23
<212> TYPE: DNA

<213> ORGANISM: Unknown
<220> FEATURE:
<223> OTHER INFORMATION: synthetic

<400> SEQUENCE: 64
tttatcgtcg accactgtgc tgg 23

<210> SEQ ID NO 65
<211> LENGTH: 24
<212> TYPE: DNA
<213> ORGANISM: Unknown
<220> FEATURE:
<223> OTHER INFORMATION: synthetic

<400> SEQUENCE: 65
cctccgggac atgatcagca tgta 24

<210> SEQ ID NO 66
<211> LENGTH: 20
<212> TYPE: DNA
<213> ORGANISM: Unknown
<220> FEATURE:
<223> OTHER INFORMATION: synthetic

<400> SEQUENCE: 66
cggcatcacg gtttttgcgt 20

<210> SEQ ID NO 67
<211> LENGTH: 24
<212> TYPE: DNA
<213> ORGANISM: Unknown
<220> FEATURE:
<223> OTHER INFORMATION: synthetic

<400> SEQUENCE: 67
cctccgggac atgatcagca tgta 24

<210> SEQ ID NO 68
<211> LENGTH: 23
<212> TYPE: DNA
<213> ORGANISM: Unknown
<220> FEATURE:
<223> OTHER INFORMATION: synthetic

<400> SEQUENCE: 68
tttatcgtcg accactgtgc tgg 23

<210> SEQ ID NO 69
<211> LENGTH: 27
<212> TYPE: DNA
<213> ORGANISM: Unknown
<220> FEATURE:
<223> OTHER INFORMATION: synthetic

<400> SEQUENCE: 69
tcaaccaccc cttctctatc aacaacc 27

<210> SEQ ID NO 70
<211> LENGTH: 26
<212> TYPE: DNA
<213> ORGANISM: Unknown
<220> FEATURE:
<223> OTHER INFORMATION: synthetic

<400> SEQUENCE: 70
tgggtagtgc atgacctgtt cgtagg 26

<210> SEQ ID NO 71
<211> LENGTH: 23
<212> TYPE: DNA
<213> ORGANISM: Unknown
<220> FEATURE:
<223> OTHER INFORMATION: synthetic

<400> SEQUENCE: 71
gatcccttcc gacagggtct cac 23

<210> SEQ ID NO 72
<211> LENGTH: 20
<212> TYPE: DNA
<213> ORGANISM: Unknown
<220> FEATURE:
<223> OTHER INFORMATION: synthetic

<400> SEQUENCE: 72
agactgcctt gggaaaagcg 20

<210> SEQ ID NO 73
<211> LENGTH: 27
<212> TYPE: DNA
<213> ORGANISM: Unknown
<220> FEATURE:
<223> OTHER INFORMATION: synthetic

<400> SEQUENCE: 73
tcaaccaccc cttctctatc aacaacc 27

<210> SEQ ID NO 74
<211> LENGTH: 20
<212> TYPE: DNA
<213> ORGANISM: Unknown
<220> FEATURE:
<223> OTHER INFORMATION: synthetic

<400> SEQUENCE: 74
agactgcctt gggaaaagcg 20

METHODS AND COMPOSITIONS FOR SELECTIVE GENERATION OF DOPAMINERGIC PRECURSORS

CROSS REFERENCE TO RELATED APPLICATION

This application is the U.S. National Phase of PCT Application No. PCT/CN2015/087503, filed on Aug. 19, 2015, which claims priority to and the benefit of U.S. Application No. 62/038,914 filed on Aug. 19, 2014, the contents of which are incorporated herein by reference in their entirety.

STATEMENT OF GOVERNMENT SUPPORT

This invention was made with government support under Grant Nos. R01 N5418580 and R01 N5061642 awarded by the National Institutes of Health. The government has certain rights in the invention.

This invention was also made with government support under Grant Nos. 81271419, 81028007, and 81329002 from the National Natural Science of China; and under Grant No. 2014CB965001 from the National Basic Research Program of China. The Chinese government also has certain rights in the invention.

FIELD OF THE INVENTION

The invention in general relates to methods and compositions for transdifferentiation of a somatic cell, e.g., a fibroblast to a dopaminergic precursor. Particularly, the invention relates to an induced dopaminergic precursor (iDP) cell, master transcription factors (TFs) therefor, methods for making iDP cells, and methods and compositions for using them in, e.g., treating neurodegenerative diseases such as Parkinson's disease.

BACKGROUND OF THE INVENTION

Selective degeneration of functional neurons is a key pathogenic event in many neurodegenerative disorders. Cell replacement through transplantation of stem/progenitor cells represents a particularly promising therapeutic strategy for these diseases. One of the most sought after diseases for cell replacement is Parkinson's disease (PD), which is a prototypical illness characterized by the loss of dopaminergic (DA) neurons in the substantia nigra pars compacta (SNpc) and decreased DA innervation in the striatum[1,2]. Recent breakthroughs in stem cell biology have established the feasibility of directly reprogramming cells of one lineage into another, e.g., neurons, by introducing crucial cell-fate determinants[3,4]. As a result of those advances, induced neurons[5-9] and induced neural stem cells (iNPCs)[10-13] have been successfully generated, and studies show that these cells hold therapeutic benefits. Direct reprogramming represents an important direction to obtain safe and less controversial cell sources for PD treatment. However, the low yield and non-proliferative nature of dopaminergic neurons derived from direct reprogramming limits broad application. Multipotent neural stem/progenitor cells (NSC/NPC), including iNPCs that give rise to all types of neural cells, may increase the yield of engraftable cells; however, specific and efficient induction of homogeneous DA neurons from NPCs/iNPCs remains a significant challenge. NSCs/NPCs often respond poorly to pre-patterning morphogens with low differentiation efficiency for specific neuronal subtypes, and are prone to a glial-restricted state[14]. Moreover, grafted NSCs/NPCs are more likely to terminally differentiate into astrocytes rather than functional neurons in response to injury[15,16]. Therefore, dopaminergic neuronal-lineage restricted precursors that hold great potential for DA neuronal differentiation are highly desirable for experimental PD treatment.

Thus, a need exists for dopaminergic precursors, in particularly in vitro induced dopaminergic precursors (iDP). Studies have previously revealed that Brn2/Brn4 and Sox2 are critical for the direct conversion of fibroblasts into induced neural progenitors[9,10,13,17]. Strategically, various groups have been working on the direct reprogramming of somatic cells into region-specific iNPCs as well as subtype-specific iNPCs by expressing defined transcript factors in addition to Brn2/Brn4 and Sox2[10,18]. The factors that directly reprogram somatic cells into neuronal lineage-restricted progenitors have been expanded to the combination of Brn2/Brn4 and Sox2 with c-Myc[19]. In addition, in the presence of Brn2 and Sox2, FoxG1, a transcription factor that is predominantly expressed in the forebrain, contributes to the acquisition of forebrain identity in iNPCs[10]. In contrast, the midbrain DA neurons that originated from the floor plate cells in the mesencephalon are critically regulated by transcriptional determinants such as Foxa2[20-22]. Furthermore, the development of DA neurons depends not only on initial Sonic hedgehog (SHH)/Fibroblast growth factor 8 (FGF8) and Wnt1 signaling pathway for the dopaminergic progenitors, but also on the cooperation of SHH-Foxa2 and Wnt1-Lmx1α pathways[23]. However, before the discovery herein, no complete panel of transcription factors have been identified to be able to transdifferentiate somatic cells into iDPs in vitro. In contrast, the derivation of engraftable DPs from human pluripotent stem cells has proven difficult due to low differentiation efficiency of DA neurons and primary DPs are not readily available.

SUMMARY OF THE INVENTION

In one aspect, the present invention provides an induced dopaminergic precursor (iDP), comprising ectopically expressed genes and/or proteins selected from: (1) one or both of Brn2 and Brn4, (2) Sox2, and (3) one or both of Foxa2 and Lmx1a, or a variant of any one or more of the foregoing, in a somatic cell that is not dopaminergic precursor. The gene or its variant can be the full-length gene, a fragment thereof or the cDNA, optionally under the control of a constitutive or conditional promoter.

In some embodiments, the iDP includes ectopically expressed Brn2, Sox2 and Foxa2, or a variant of any one or more of the foregoing. The ectopically expressed genes can be expressed from one or more vectors carrying them, or the ectopically expressed proteins can be expressed from one or more mRNA encoding them. In various embodiments, the iDP is a dopaminergic neuronal lineage-restricted progenitors and does not differentiate into a glial cell. In certain embodiments, differentiation of the iDP is independent of morphogens selected from SHH and FGF8. The iDP in some examples can further include ectopically expressed L-Myc, which is optionally conditionally expressed under the control of doxycycline. In some embodiments, the somatic cell is a fibroblast. The somatic cell can be present in vitro.

The iDP disclosed and claimed herein can be used in a treatment of a neurodegenerative disease selected from Parkinson's disease, depression, dementia and schizophrenia.

In another aspect, provided herein is a population of the iDPs disclosed herein, wherein more than 80% or more than 90% of the iDPs are capable of differentiating into dopaminergic neurons.

In yet another aspect, a method of transdifferentiating a somatic cell to an iDP is provided, comprising ectopically expressing genes selected from: (1) one or both of Brn2 and Brn4, (2) Sox2 and (3) one or both of Foxa2 and Lmx1a, or a variant of any one or more of the foregoing, in a somatic cell that is not dopaminergic precursor.

In some embodiments, the method includes ectopically expressing Brn2, Sox2 and Foxa2, or a variant of any one or more of the foregoing, in the somatic cell. The somatic cell may be a fibroblast. The somatic cell can be present in vitro. The somatic cell can be obtained from a patient in need of cell or tissue replacement therapy with iDP. The patient can have Parkinson's disease, depression, dementia or schizophrenia.

Also provided herein is a method of treating a neurodegenerative disease, comprising administering to a patient in need thereof the iDP disclosed herein.

A further aspect relates to a method of identifying an agent that regulates dopaminergic neuron development, comprising subjecting a population of the iDPs disclosed herein to a test agent, wherein a change in differentiation of the iDPs to dopaminergic neuron is indicative of a regulatory role of the test agent in dopaminergic neuron development. In some embodiments, the change is one or more of: cell growth, cell survival, or gene expression change in one or more of tyrosine hydroxylase (TH), Sox1, PAX6, ZBTB16, Sox3, CD133, Nestin, Aldh1A1, Corin (Lrp4), Lmx1a, Msx1, Ngn2, Otx2, Mash1, Pitx3 and Nkx6.1, ploysialic acid-neural cell adhesion molecule (PSA-NCAM), and/or doublecortin (DCX). In certain embodiments, the iDPs are transdifferentiated from a patient's somatic cells, wherein the patient has Parkinson's disease, depression, dementia or schizophrenia, and wherein the method identifies agents for the treatment of Parkinson's disease, depression, dementia or schizophrenia.

Another aspect relates to a composition comprising one or more vectors carrying isolated genes selected from: (1) one or both of Brn2 and Brn4, (2) Sox2 and (3) one or both of Foxa2 and Lmx1a, or a variant of any one or more of the foregoing. In some embodiments, the one or more vectors can carry Brn2, Sox2 and Foxa2, or a variant of any one or more of the foregoing. The vector is a viral vector.

It is to be understood that both the foregoing general description and the following detailed description are exemplary and explanatory only and are not restrictive or limiting the scope of the invention described and claimed herein.

BRIEF DESCRIPTION OF THE FIGURES

FIG. 6B) One week after MPTP intoxication, $GFP^+$ iDPs were intracranially injected into the striatum of C57BL/6 mice. Free-floating sections of brain specimens were prepared 3 weeks after iDPs engraftment. Representative photomicrographs of striatum after PBS injection (a), MPTP intoxication with saline IC injection (b), and MPTP with iDPs IC injection (c) were shown. Striatal $TH^+$ densities of DA termini were quantified and data represent means±SEM of striatal densities. Four striatal sections from each mouse were used for analysis. N=10 mice for saline IC injection group; N=7 mice for MPTP group and MPTP with iDPs IC injection group. FIG. 6C) Survival and differentiation of $GFP^+$ iDPs following IC injection into the striatum of mice were evaluated 3 weeks post-IC injection. FIG. 6D) The grafted cells were detected by immunostaining with antibodies against GFP, TH and GFAP (red), and nuclear staining with DAPI (blue). (Scale bars: 20 μm)

Mice were tested twice a week with rotarod motor function tests for 3 weeks following iDPs engraftment. FIG. 7A) Pre-MPTP performance values for all mice group were determined with rotarod. FIG. 7B) Weekly performance values for all mice group at week 2 were shown. FIG. 7C) Weekly performance values for all mice group at week 1-3 were shown. Data represent means±SEM of each group normalized to baseline rotarod performance. Statistical analysis was performed using two-tailed Student's t tests. N=10 mice for saline IC injection group; N=7 mice for MPTP group and MPTP with iDPs IC injection group.

Real-time RT-PCR analysis of iDPs employing specific primer pairs for the detection of transgenic genes (FIG. 10A) and endogenous genes (FIG. 10B) used for iDP generation including Brn2, Sox2 and Foxa2. GAPDH-specific primer pairs were used for internal control; Fbb served as negative control and WT-NPCs served as positive control for endogenous detection.

Figure 11:
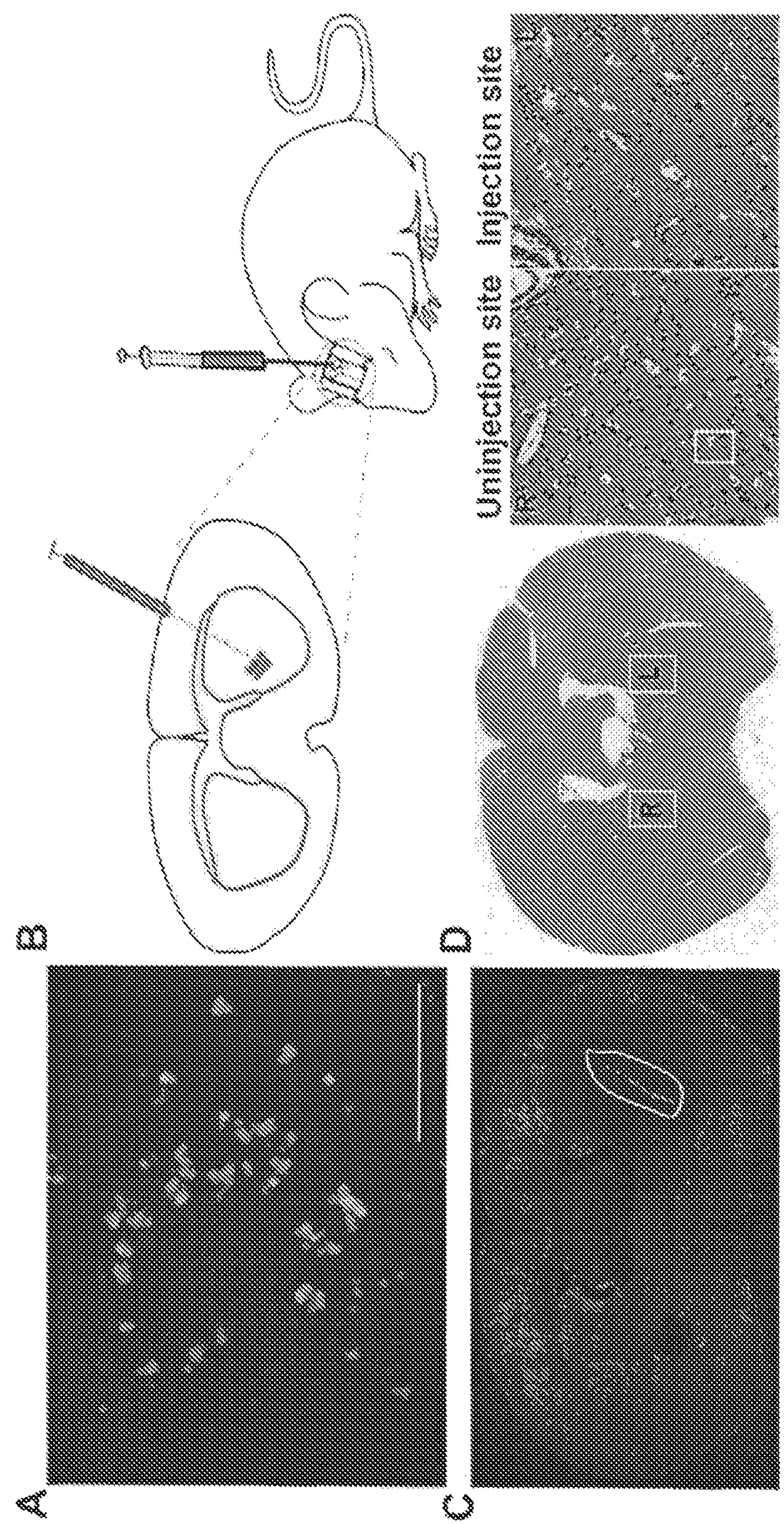

FIGS. 11A-11D. Cell injection, survival and safe evaluation of iDPs in SCID mice iDPs were infected with pLenti-CMV-GFP-Puroviruses and screened with puromycin (FIG. 11A). Schematic diagram of stereotactic injection of GFP-labeled iDPs in SCID mice (FIG. 11B). GFP-labeled iDPs were intracranially injected into the striatum of SCID mouse brain and images were captured using Leica confocal microscope and Metamorph analysis software (Molecular Devices) (FIG. 11C). Paraffin sections of formlin-fixed brain specimens were prepared 6 weeks after injection, and hematoxylin and eosin (H.E) staining shows tissues in injected (L, Left) and un-injected (R, Right) sides by Ventana's Coreo Au Slider Scanner (FIG. 11D).

Figure 12:
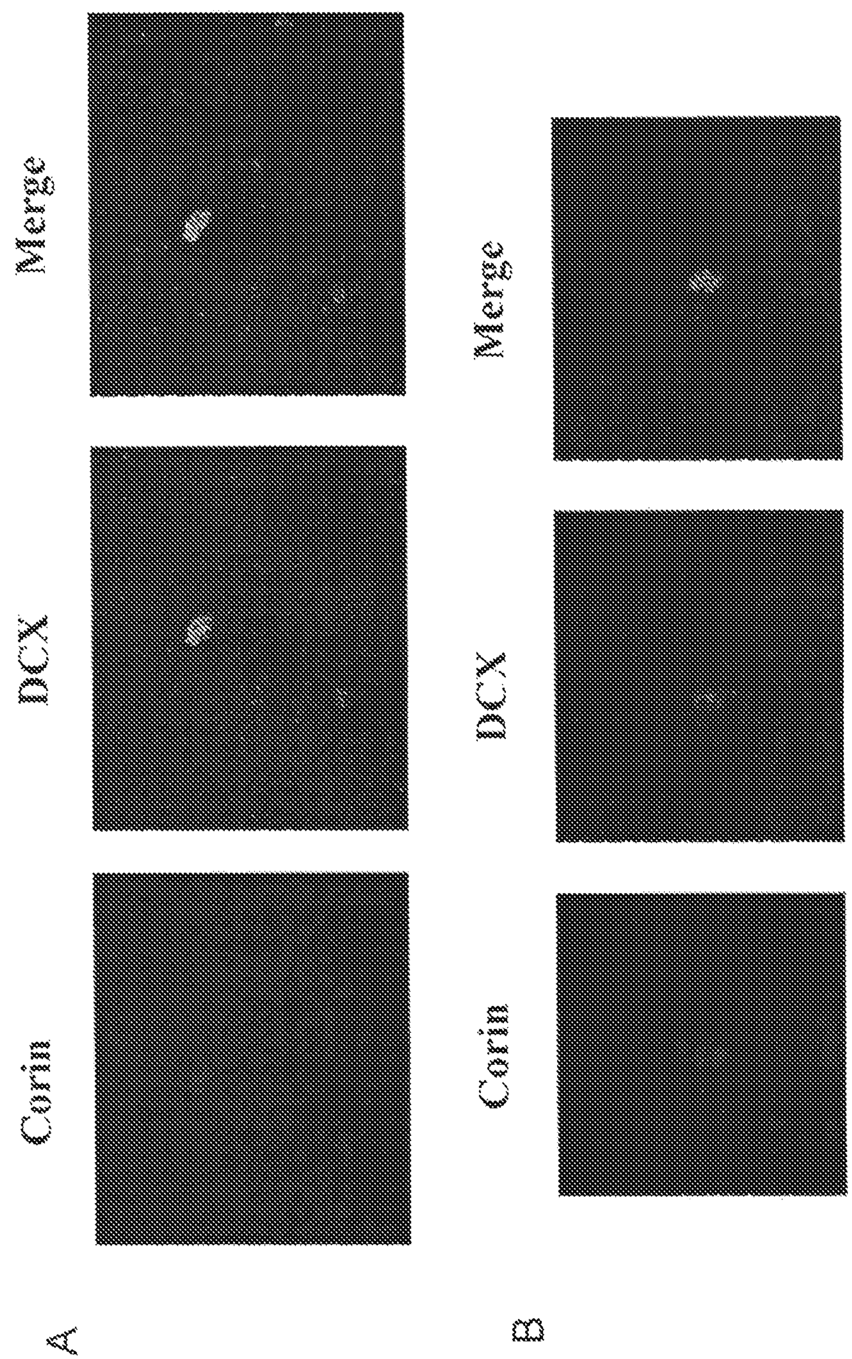

FIGS. 12A-12B. Characterizations of iDPs derived from a PD patient (FIG. 12A) and a 105d fetus (FIG. 12B). Colocalization of Corin (left panel) and DCX (middle panal) in iDPs cells.

DETAILED DESCRIPTION OF THE INVENTION

Compositions and methods for transdifferentiation of a somatic cell, e.g., a fibroblast to a dopaminergic precursor (DP) are disclosed herein. In one aspect, it was surprisingly discovered, for the first time in vitro, that the specification of midbrain identity and dopaminergic neural fate can be achieved by the ectopic expression of Brn2 (and/or Brn4) and Sox2 with Foxa2 (and/or Lmx1a) during the direct reprogramming of terminally differentiated cells. It is particularly unexpected that a high percentage (e.g., more than 80% or more than 90%) of the cells can be transdifferentiated into iDPs in cells ectopically expressing Brn2, Sox2 and Foxa2. In some embodiments, the addition of Foxa2 (and/or Lmx1a) into the reprogramming procedure initiated by Brn2 (and/or Brn4) and Sox2 successfully converts adult skin fibroblasts into neural progenitors with a midbrain identity and selective dopaminergic differentiation potential. As a result, the induced DPs (iDPs) are dopaminergic neuronal-restricted in vitro and in vivo, and do not form tumors or neural overgrowths in the brain. Moreover, grafted iDPs in the striatum of MPTP mouse model differentiated terminally into DA neurons rather than astrocytes, and functionally alleviate PD symptoms. Furthermore, L-Myc expression can be engineered in the iDPs under the control of an inducer, e.g., doxycycline (Dox), such that the iDPs can be safely expanded to the desired yield for transplantation, providing a useful cell source for PD treatment.

In some embodiments, Brn2 (and/or Brn4), Sox2 and Foxa2 (and/or Lmx1a ) are the master transcription factors that can be used to induce transdifferentiation of a somatic cell to iDP by, e.g., ectopically expressing the master transcription factors in the somatic cell. The resulting iDPs not only exhibit the properties of primary dopaminergic progenitors, but also exclusively possess the dopaminergic neuronal lineage-restricted potential. The iDPs can be used in a cell or tissue replacement therapy for the treatment of a neurodegenerative disease such as Parkinson's disease, schizophrenia, depression and dementia. In some embodiments, autologous somatic cells obtained from a patient are subject to transdifferentiation, so that the resulting cells can be transplanted back to the same patient to minimize immune response that might otherwise be mounted against the cells and to avoid the potential need for immunosuppression.

Some of the advantages of the present disclosure over the currently available technologies include the following:

1. The ectopic expression of certain transcription factors disclosed herein can lead to exclusive dopaminergic neuronal lineage-restricted progenitors that do not differentiate into glial cells. In contrast, most of the existing stem cells have been found to differentiate into glial cells. Thus, the iDPs of the present disclosure provide increased therapeutic efficiency compared to other technologies.

2. Unlike other precursors, the differentiation of the iDPs of the present disclosure is, surprisingly, independent of morphogens such as SHH and FGF8. In contrast, other precursors studied to date all require morphogens to induce differentiation.

3. The iDPs disclosed herein have higher potential and efficiency of dopaminergic neuron generation (e.g., more than 80% or more than 90%), compared to currently available technologies which only range from 5% to 60%.

4. The iDPs can be further modified (e.g., by transducing L-Myc expression) so as to have limited proliferation, reducing tumorigenicity after cell transplantation.

Definitions

For convenience, certain terms employed herein, in the specification, examples and appended claims are collected here. Unless otherwise defined, all technical and scientific terms used herein have the same meaning as commonly understood by one of ordinary skill in the art to which this disclosure belongs.

The term "transdifferentiation" or "transdifferentiating" is used interchangeably herein with the phrase "reprogramming" and refers to the conversion of one differentiated somatic cell type into a different differentiated somatic cell type.

As used herein, the term "somatic cell" refers to any cells forming the body of an organism, as opposed to germline cells. In mammals, germline cells include the gametes (spermatozoa and ova) which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. Unless otherwise indicated the methods for direct conversion of a somatic cell, e.g., fibroblast to an iDP cell can be performed both in vivo and in vitro (where in vivo is practiced when a somatic cell, e.g., fibroblast, is present within a subject, and where in vitro is practiced using isolated somatic cell, e.g., fibroblast, maintained in culture).

The term "dopaminergic precursor" or "dopaminergic progenitor" or "DP" refers to post-mitotic cells that migrate ventrally from the ventricular zone along radial glia to their final destinations in the tegmental mantle layer. During their migration, they start to express tyrosine hydroxylase (TH), the rate-limiting enzyme in dopamine synthesis, and eventually differentiate into dopaminergic neurons. A group of the dopaminergic neurons are involved in control of voluntary movement and are severely affected in Parkinson's disease. Another group of the dopaminergic neurons are involved in regulation of emotion-related behavior and are affected in depression and schizophrenia. Thus, iDP cells can be used to treat these diseases by, e.g., transplantation or cell replacement therapy.

As used herein, the term "endogenous DP cell" refers to a DP cell in vivo or a DP cell produced by differentiation of an embryonic stem cell into a DP cell, and exhibiting a DP cell phenotype. The phenotype of a DP cell is well known by persons of ordinary skill in the art, and includes, for example, gene expression signature, e.g., tyrosine hydroxylase (TH), Sox1, PAX6, ZBTB16, Sox3, CD133, Nestin, Aldh1A1, Corin (Lrp4), Lmx1a, Msx1, Ngn2, Otx2, Mash1, Pitx3 and Nkx6.1, ploysialic acid-neural cell adhesion molecule (PSA-NCAM), doublecortin (DCX), and/or dopaminergic neuronal lineage-restricted differentiation potential.

The term "induced dopaminergic precursor cell" or "iDP cell" as used herein refers to a DP or DP-like cell having one or more DP characteristics (e.g., morphology, gene expression, and function) produced by direct conversion from a somatic cell, e.g., a fibroblast.

The term "ectopic" refers to a substance present in a cell or organism other than its native or natural place and/or level. For example, the term "ectopic expression" refers to the expression of a gene in an abnormal or non-natural place (e.g., cell, tissue or organ), and/or at an abnormal (increased or decreased) level in an organism or in vitro culture.

The term "expression" refers to the cellular processes involved in producing RNA and proteins, including where applicable, but not limited to, for example, transcription, translation, folding, modification and processing. "Expression products" include RNA transcribed from a gene and polypeptides obtained by translation of mRNA transcribed from a gene.

As used herein, "Brn2", "Brn4", "Sox2", "Foxa2" and "Lmx1a" refer to Genbank accession Nos.: NM_005604 (human), NM_000307 (human), NM_003106.3 (human), NM_021784.4 (human), and NM_001174069.1 (human), respectively. These terms also encompass species variants, homologues, allelic forms, mutant forms, and equivalents thereof, including conservative substitutions, additions, deletions therein not adversely affecting the structure or function. In addition to naturally-occurring allelic variants of the sequences that may exist in the population ("wild-type sequences"), it will be appreciated that, as is the case for virtually all proteins, a variety of changes can be introduced into the wild-type sequences without substantially altering the functional (biological) activity of the polypeptides. Such variants are included within the scope of the terms "Brn2", "Brn4", "Sox2", "Foxa2" and "Lmx1a". Mouse and human Brn2, Brn4, Sox2, Foxa2 and Lmx1a sequences are listed in Table 1 below.

TABLE 1

| Exemplary Sequences | | |
|---|---|---|
| Gene | Mouse | Human |
| Brn2 | SEQ ID NO.: 1 | SEQ ID NO.: 6 |
| Brn4 | SEQ ID NO.: 2 | SEQ ID NO.: 7 |
| Sox2 | SEQ ID NO.: 3 | SEQ ID NO.: 8 |
| Foxa2 | SEQ ID NO.: 4 | SEQ ID NO.: 9 |
| Lmx1a | SEQ ID NO.: 5 | SEQ ID NO.: 10 |

As used herein, the term a "variant" in referring to a polypeptide could be, e.g., a polypeptide at least 80%, 85%, 90%, 95%, 98%, or 99% identical to full length polypeptide. The variant could be a fragment of full length polypeptide, e.g., a fragment of at least 10 or at least 20 contiguous amino acids of the wild type version of the polypeptide. In some embodiments, a variant is a naturally occurring splice variant. The variant could be a polypeptide at least 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof having an activity of interest such as the ability to directly convert fibroblasts to iDP cells. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein.

One of skill in the art will be aware of, or will readily be able to ascertain, whether a particular polypeptide variant, fragment, or derivative is functional using assays known in the art. For example, the ability of a variant of a Brn2, Brn4, Sox2, Foxa2 and/or Lmx1a polypeptide to convert a somatic cell, e.g., fibroblast to an iDP can be assessed using the assays as disclose herein. Other convenient assays include measuring the ability to activate transcription of a reporter construct containing a Brn2, Brn4, Sox2, Foxa2 and/or Lmx1a variant operably linked to a nucleic acid sequence encoding a detectable marker such as florescent protein or luciferase. One assay involves determining whether the Brn2, Brn4, Sox2, Foxa2 and/or Lmx1a variant induces a somatic cell, e.g., fibroblast to become an iDP cell or express markers of a DP cell or exhibit functional characteristics of a DP cell as disclosed herein. Determination of such expression of DP markers can be determined using any suitable method, e.g., immunoblotting or real-time quantitative reverse transcription (RT)-PCR. Such assays may readily be adapted to identify or confirm activity of agents that directly convert a somatic cell, e.g., fibroblast to an iDP cell. In certain embodiments of the disclosure a functional variant or fragment has at least 50%, 60%, 70%, 80%, 90%, 95% or more of the activity of the full length wild type polypeptide.

As used herein, the term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operably linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

As used herein, the term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or HeDPs simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g. EPV and EBV vectors.

As used herein, the term "transcription factor" refers to a protein that binds to specific parts of DNA using DNA binding domains and is part of the system that controls the transfer (or transcription) of genetic information from DNA to RNA.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms "subject" and "individual" and "patient" are used interchangeably herein, and refer to an animal, for example, a human from whom cells can be obtained and/or to whom treatment, including prophylactic treatment, with the cells as described herein, is provided. For treatment of those conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g., dog, cat, horse, and the like, or production mammal, e.g., cow, sheep, pig, and the like.

The terms "treat", "treating", "treatment", etc., as applied to an isolated cell, include subjecting the cell to any kind of process or condition or performing any kind of manipulation or procedure on the cell. As applied to a subject, the term "treating" refer to providing medical or surgical attention, care, or management to an individual. The individual is usually ill or injured, or at increased risk of becoming ill relative to an average member of the population and in need of such attention, care, or management. In some embodiments, the term "treating" and "treatment" refers to administering to a subject an effective amount of a composition, e.g., a composition comprising iDP cell or their differentiated progeny so that the subject has a reduction in at least one symptom of the disease or an improvement in the disease, for example, beneficial or desired clinical results. For purposes of this disclosure, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. In some embodiments, treatment can be "prophylactic" treatment, where the subject is administered a composition as disclosed herein (e.g., a population of iDP cell or their progeny) to a subject at risk of developing a neurodegenerative disease as disclosed herein. In some embodiments, treatment is "effective" if the progression of a disease is reduced or halted. Those in need of treatment include those already diagnosed with a neurodegenerative disease or disorder, e.g., Parkinson's disease (PD), as well as those likely to develop a neurodegenerative disease or disorder due to genetic susceptibility or other factors such as family history, exposure to susceptibility factors, weight, age, diet and health.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

As used herein, the term "about" means within 20%, more preferably within 10% and most preferably within 5%.

As used herein, the word "a" can also mean "any."

As used herein, the term "or" can include the meanings of both "or" and "and"—depending on the context and underlying technical situation—and may be interchanged with "and/or."

It is understood that the detailed description and the examples provided herein are illustrative only and are not to be taken as limitations upon the scope of the invention. Various changes and modifications to the disclosed embodiments, which will be apparent to those of skill in the art, may be made without departing from the spirit and scope of the present disclosure. Further, all patents, patent applications, and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

Somatic Cells

While fibroblasts are generally used, essentially any primary somatic cell type can be substituted for a fibroblast with the methods described herein. Some non-limiting examples of primary cells include, but are not limited to, epithelial, endothelial, neuronal, adipose, cardiac, skeletal muscle, immune cells, hepatic, splenic, lung, circulating blood cells, gastrointestinal, renal, bone marrow, and pancreatic cells. The cell can be a primary cell isolated from any somatic tissue including, but not limited to brain, liver, lung, gut, stomach, intestine, fat, muscle, uterus, skin, spleen, endocrine organ, bone, etc.

Where the cell is maintained under in vitro conditions, conventional tissue culture conditions and methods can be used, and are known to those of skill in the art. Isolation and culture methods for various cells are well within the abilities of one skilled in the art.

Further, the parental cell can be from any mammalian species, with non-limiting examples including a murine, bovine, simian, porcine, equine, ovine, or human cell. For clarity and simplicity, the description of the methods herein refers to fibroblasts as the parental cells, but it should be understood that all of the methods described herein can be readily applied to other primary parent cell types. In some embodiments, the somatic cell is derived from a human individual.

In some embodiments, the methods and compositions of the present disclosure can be practiced on somatic cells that are fully differentiated and/or restricted to giving rise only to cells of that particular type. The somatic cells can be either partially or terminally differentiated prior to direct conversion to iDPs or other cell types of interest. In some embodiments, somatic cells which are trandifferentiated into iDPs or other cell types of interest are fibroblast cells.

Reprogramming (Transdifferentiation)

The process of altering the cell phenotype of a differentiated cell (i.e. a first cell), e.g., altering the phenotype of a somatic cell to a differentiated cell of a different phenotype (i.e. a second cell) is referred to as "reprogramming" or "transdifferentiation". Stated another way, cells of one type can be converted to another type in a process by what is commonly referred to in the art as transdifferentiation, direct reprogramming, cellular reprogramming or lineage reprogramming.

As disclosed herein, the present disclosure relates to compositions and methods for the direct conversion of a somatic cell, e.g., a fibroblast to iDP. Master transcription factors of iDP can include one or more of Brn2, Brn4, Sox2, Foxa2 and/or Lmx1a. In certain embodiments, the master TFs can be Brn2, Sox2 and Foxa2. In further embodiments, the master TFs can be Brn4, Sox2 and Foxa2. In some embodiments, the master TFs can be Brn2, Sox2, and Lmx1a. In some embodiments, the master TFs can be Brn4, Sox2, and Lmx1a. In some embodiments, the master TFs can be Brn2, Brn4, Sox2 and Foxa2. In some embodiments, the master TFs can be Brn2, Brn4, Sox2, and Lmx1a. In some embodiments, the master TFs can be Brn2, Brn4, Sox2, Foxa2 and Lmx1a.

By increasing expression level of certain master transcription factors in a somatic cell, transdifferentiation into DP can be induced. Various methods for increasing expression level known in the art can be used, including without limitation, contacting the somatic cell with an agent which increases the expression of the master transcription factors, such as a nucleotide sequence (e.g., encoding one or more of the master transcription factors), a protein, an aptamer, a small molecule, a ribosome, an RNAi agent, a peptide-nucleic acid (PNA), or analogues or variants thereof. In some embodiments, ectopic expression of the master transcription factors in the somatic cell induces transdifferentiation into DP. Ectopic expression can be achieved via introduction of a transgene of the transcription factor (carried by, e.g., a vector, e.g., a viral vector such as retrovirus, lentivirus, adenovirus, adeno-associated virus, and/or nanoparticles). Alternatively or additionally, endogenous gene expression can also be increased by modulating transcriptional machinery such as activating its corresponding promoters and/or enhancers, recruiting transcription factors and/or RNA polymerase to the promoter/enhancer region, de-activating silencers, decreasing or removing repressors, etc. In some embodiments, epigenetic modification of the chromatin structure can be used to enhance endogenous gene expression.

In some embodiments, nucleic acids encoding multiple master TFs (e.g., 2, 3, 4, or more) may be incorporated into a vector under control of separate promoters or under control of the same promoter. For example, a polycistronic vector in which nucleic acid sequences encoding the polypeptides are separated by 2A peptides or IRES sequences may be used. Those of ordinary skill in the art are aware of 2A peptides, IRES sequences, and their use to co-express multiple polypeptides in cells, where the multiple polypeptides are encoded by a single mRNA. See, e.g., US Patent Application Pub. No. 20120028821 for further description of 2A peptides and their use to co-express multiple polypeptides in cells. In some embodiments, a transgene comprising a nucleic acid encoding the TF(s) may be integrated at a selected location such as a safe harbor locus (e.g., the adeno-associated virus integration site 1 (AAVS1) in human cells. In some embodiments, integration of a nucleic acid at a selected location in the genome may be achieved using genome editing systems such as CRISPR/Cas9, TALENs, or zinc finger nucleases.

In some embodiments, ectopic expression of one or more master TFs may be achieved by introducing synthetic modified mRNA encoding the TF(s) into the cells. In some embodiments, synthetic modified mRNA comprises one or more nucleotides that are not normally found in naturally occurring mRNA encoding the master TFs. Such nucleotides may, for example, enhance stability and/or translation of the synthetic mRNA. Those of ordinary skill in the art are aware of suitable types of synthetic modified mRNA useful for expressing proteins in cells. See, e.g., US 2012/0046346 and WO 2011/130624, both of which are incorporated herein by reference in their entireties.

In certain embodiments, compositions and methods for transdifferentiation of a somatic cell, e.g., a fibroblast to a functional DP cell, referred to herein as an "induced DP (iDP) cell" are provided. In certain embodiments, the transdifferentiation of a somatic cell, e.g., fibroblast causes the somatic cell to assume a DP-like state. Transdifferentiation into iDP cells can be achieved by increasing expression level of one or more of: Brn2, Brn4, Sox2, Foxa2 and Lmx1a. In some embodiments, increased expression of at least two of, at least three of, at least four of, or at least five of Brn2, Brn4, Sox2, Foxa2 and Lmx1a induces transdifferentiation of somatic cells into iDP cells. In one example, Brn2/Brn4, Sox2, and Foxa2/Lmx1a are master TFs sufficient for establishment and/or maintenance of DP cell state.

Transdifferentiated cells have many clinical, therapeutic, and scientific applications. In some embodiments, the transdifferentiated cells can be transplanted to a patient in need of cell replacement therapy. The cells can be autologous to the patient, i.e., somatic cells from the patient can be first obtained, induced in vitro to transdifferentiate into iDPs, and then transplanted back to the same patient. In one example, iDP cells can be transplanted to treat Parkinson's disease or other diseases such as depression, schizophrenia and dementia. In other embodiments, transdifferentiated cells can be cultured in vitro and/or subject to various in vitro experiments as a model for improving viability and/or to study their properties, and can be used to produce a substance (e.g., a protein) of interest or to generate artificial tissue/organ.

In some embodiments, cells that express one or more of the master TFs described herein may be used in methods (e.g., screening methods) to identify agents (e.g., small molecules (organic molecules having a molecular weight of 1.5 kilodaltons or less), nucleic acids (e.g., RNAi agents, microRNAs), or polypeptides) that may be used in a method of generating iDP cells to increase the efficiency of direct reprogramming and/or used instead of one or more of the master TFs described herein (as a substitute for one or more of the master TFs described herein) and/or to increase the efficiency of direct reprogramming. For example, in certain embodiments a population of somatic cells expressing one or more of the master TFs described herein is contacted with a test agent, and the ability of the test agent to increase the efficiency and/or speed of direct reprogramming to iDP is determined. Efficiency of direct reprogramming can be measured as the number of colonies of transdifferentiated cells of iDP cells that arise from a given number of somatic cells of a different cell type (e.g., fibroblasts) that have modified to cause increased expression of one or more of the master TFs for the iDP.

In some embodiments, iDP cells (and/or dopaminergic neurons produced therefrom) may be used as model systems, which may be used, e.g., for testing the potential efficacy and/or toxicity of agents such as candidate therapeutic agents or otherwise to evaluate the effect of agents or environmental conditions on the cells.

iDP Production

Degeneration of midbrain dopaminergic (DA) neurons is a key pathological event of Parkinson's disease (PD). Limited adult dopaminergic neurogenesis has led to novel therapeutic strategies such as transplantation of dopaminergic precursors (DPs). However, this strategy is currently restrained by a lack of cell source, the tendency for the DPs to become a glial-restricted state, and the tumor formation after transplantation. Here, we demonstrate the direct conversion of mouse fibroblasts into induced DPs (iDPs) by ectopic expression of Brn2, Sox2 and Foxa2. Besides expression with neural progenitor markers and midbrain genes including Corin, Otx2 and Lmx1a, the iDPs were restricted to dopaminergic neuronal lineage upon differentiation. After transplantation into MPTP-lesioned mice, iDPs differentiated into DA neurons, functionally alleviated the motor deficits, and reduced the loss of striatal DA neuronal axonal termini. Importantly, no iDPs-derived astroctyes and neoplasia were detected in mouse brains after transplantation. We propose that the iDPs from direct reprogramming provides a safe and efficient cell source for PD treatment.

Figure 8:
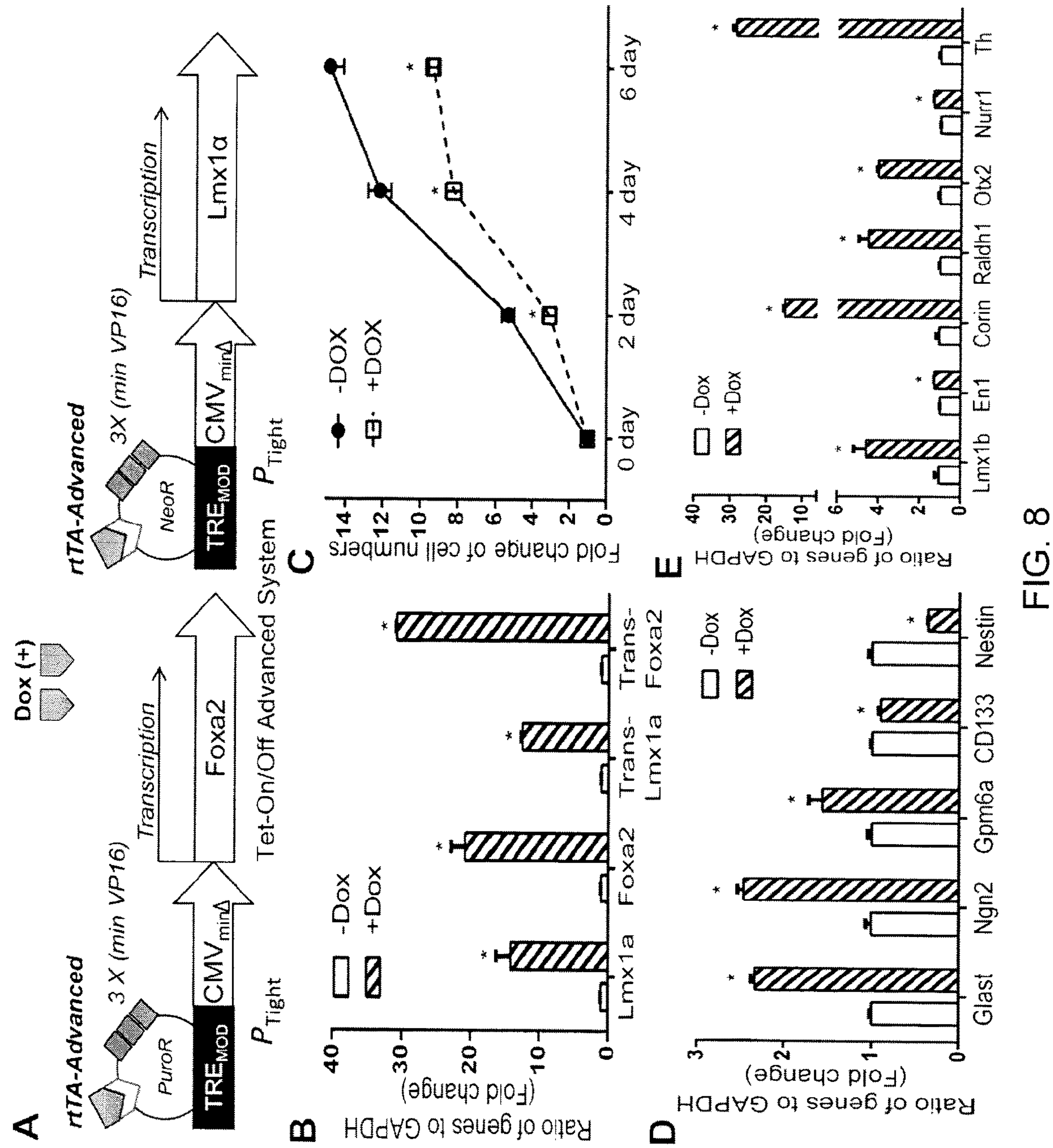
FIGS. 8A-8D. Ectopic expression of Lmx1a and Foxa2 inhibits the proliferation of 5F-iNPCs and confers the mesencephalic regional identity on 5F-iNPCs Schematic diagram of Tet-On/Off advanced system for Lmx1α and Foxa2 overexpression in 5F-iNPCs (FIG. 8A). Infected 5F-iNPCs were treated with Dox (+) and Dox (−) media for 4 days, and the total and transgene levels of Lmx1a and Foxa2 in 5F-iNPCs were investigated through real-time RT-PCR with specific primers (see Table 2) (FIG. 8B). $1\times10^5$ 5F-iNPCs were cultured in the 6-well plate with or without Dox, respectively, and the cell numbers were counted at day 2, day 4, and day 6 (FIG. 8C). 5F-iNPCs were cultured with or without Dox (1 μg/ml) for 4 days, and mRNA were collected and then subjected to real-time RT-PCR with specific primers for glial lineage, neuronal lineage and dopaminergic neuron-related genes (FIG. 8D). GAPDH-specific primer pairs were used for internal control. *denotes $p<0.05$.
Figure 9:
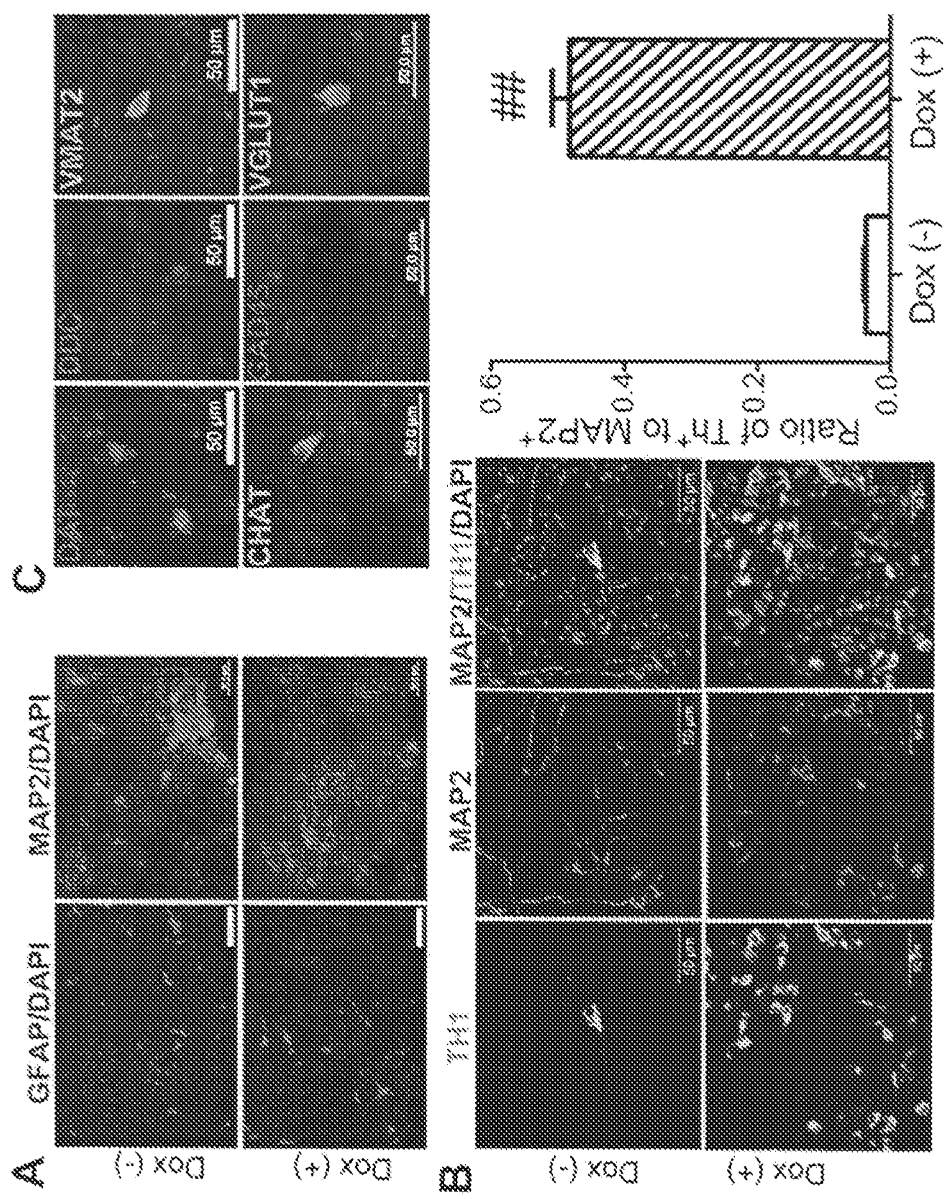
FIGS. 9A-9B. Overexpression of Lmx1α and Foxa2 increases the $TH^+$ cell population, but has minimum effect on gliogenesis 5F-iNPCs with Dox-regulatable Lmx1α and Foxa2 were treated either with or without Dox under astrocyte differentiation condition (DMEM/F-12 supplied with 10% FBS) for 10 days, and neuronal differentiation condition (DMEM/F12 with N2, GDNF, and BDNF) for 14 days. The differentiations of neurons and astrocytes were visualized through immunofluorescence staining with MAP2 and GFAP, respectively (FIG. 9A). 5F-iNPCs with Dox-regulatable Lmx1α and Foxa2 were differentiated into DA neurons in the presence of GDNF, BDNF, AA and either with or without Dox for 8 days. The immunofluorescence staining of MAP2 (red) and TH (green) were carried out (FIG. 9B, left panel), and the ratio of $TH^+$ to $MAP2^+$ was quantified (mean±SD) (FIG. 9B, right panel). * denotes $p<0.05$. (Scale bar: 50 μm)

Foxa2 Cooperated with Brn2 and Sox2 to Convert Mouse Fibroblasts into Neural Progenitors with Midbrain Identity Our initial studies have shown that skin fibroblasts can be successfully converted into induced neural progenitors (5F-iNPCs) by a set of transcription factors, including Brn2, Sox2, TLX, Bmi1 and c-Myc[13]. However, the dopaminergic differentiation efficiency of 5F-iNPCs in response to SHH/FGF8 stimulation remains low (<5%). The direct reprogramming of somatic cells into region-specific iNPCs as well as subtype-specific iNPCs by overexpression of defined transcript factors has become our strategy. It has been suggested that Foxa2 and Lmx1a are the major mediators of SHH and Wnt1 signaling in midbrain DA neuron development, respectively[23]. The role of these factors in cellular reprogramming remains unclear. We utilized a Tet-On/Off system to express Foxa2 and Lmx1a in 5F-iNPCs. The cells that successfully incorporated Foxa2 and Lmx1a genes were further screened with the addition of antibiotics puromycin and neomycin in the culture (FIG. 8A). In the presence of Dox, the ectopic expressions of Foxa2 and Lmx1a were induced (FIG. 8B). As expected, both Foxa2- and Lmx1a-expression significantly reduced the proliferation of 5F-iNPCs (FIG. 8C). Furthermore, the differentiation-related genes, including Ngn2 and Gpm6a for neuronal lineage and Glast for glial lineage, were significantly up-regulated. In contrast, the neural stem cell makers, such as CD133 and Nestin, were down-regulated (FIG. 8D). Interestingly, the expressions of tyrosine hydroxylase (TH) and several key factors responsible for midbrain dopaminergic neuron development in 5F-iNPCs were dramatically increased in response to Foxa2 and Lmx1a overexpression (FIG. 8E), suggesting that both Foxa2 and Lmx1a play a positive role in the determination of DA neuronal fate. The effect of Foxa2 and Lmx1a on DA neuronal fate was further confirmed by immunocytochemistry. Foxa2 and Lmx1a overexpression did not affect astrocyte differentiation and neuronal maturation (FIG. 9A). Under neuronal differentiation conditions with SHH/FGF8, the population of $TH^+$ cells was significantly increased following the overexpression of Foxa2 and Lmx1a (FIG. 9B, left panel). The percentage of $TH^+$ cells to total $MAP2^+$ cells was about 10-fold higher than those 5F-iNPCs without Foxa2 and Lmx1a overexpression (FIG. 9B, right panel). Together, these data suggested that Foxa2 may cooperate with Lmx1a to promote the mesencephalic dopaminergic neuron identity in iNPCs, without affecting the neuronal maturation and astrogliogenesis.

Figure 10:
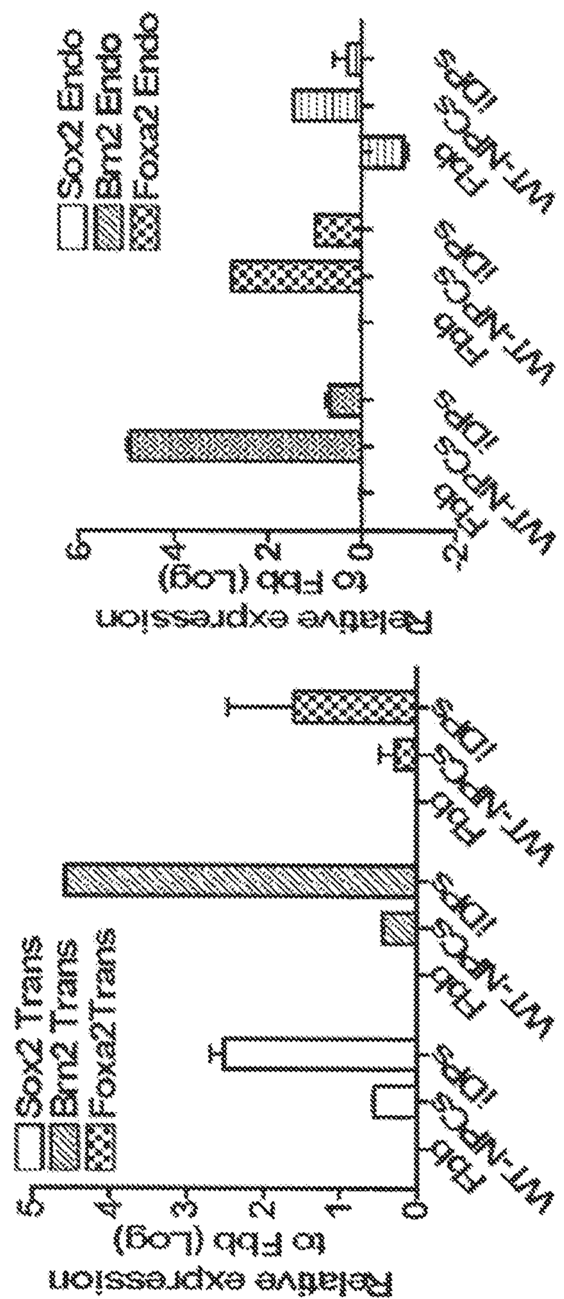
FIGS. 10A-10B. Analyses of transgenic and endogenous genes in iDPs

Although the specification and maturation of mesencephalic floor plate-originated midbrain DA neurons are primarily regulated by both Foxa2 and Lmx1a/b[24,25], recent evidence has demonstrated that Foxa2 can positively regulate Lmx1a/b and inhibit the expression of Nkx2.2 in neural progenitors[26]. This indicates that Foxa2 alone may suffice for the specification of mesencephalic dopaminergic progenitor identity. We examined this idea by determining the role of Foxa2, along with two known reprogramming factors Brn2 and Sox2, in the direct conversion of somatic cells into neural progenitors. We isolated and cultured adult dermal fibroblasts (SF) from Nestin-EGFP transgenic mice (E/Nestin: EGFP). The fibroblasts were infected with retroviruses encoding Brn2, Sox2 and Foxa2 (BSF) following a schematic procedure (FIG. 1A). The kinetics of induced neural progenitors was monitored with the EGFP in the culture. Seven days after retroviral infections, we observed EGFP positive cells in culture, and at 14 days post-infection, we observed colony formation (FIG. 1B). Seven colonies were obtained and only two were confirmed to be expandable clones after subculture. Both of the expandable clones showed identical properties (data not shown). Compared to the primary cortical neural progenitor cells (WT-NPCs), the resulting cells (named iDPs) retained high expression levels of Foxa2, Brn2 and Sox2 (FIG. 10). Meanwhile, endogenous Foxa2, Brn2 and Sox2 genes expression was also up-regulated, suggesting that the endogenous gene network had been initiated. We characterized the iDPs through the expression levels of several key neural progenitor marker genes in skin fibroblasts (Fbb), WT-NPCs and iDPs by real-time RT-PCR analysis (for sequences of the primer pairs, see Table 2). The iDPs expressed high levels of neural progenitor markers, including Sox1, PAX6, ZBTB16, Sox3, CD133 and Nestin (FIG. 1C). Importantly, the iDPs also expressed high levels of Aldh1A1, Corin (Lrp4), Lmx1a, Msx1, Ngn2, Otx2, Mash1, Pitx3 and Nkx6.1 (FIG. 1D). These genes were previously reported to specifically express in dopaminergic neuron proliferative progenitor cells[20,23,27,28]. In contrast, unlike the primary forebrain neural progenitors (NPs), the iDPs expressed the minimum levels of FoxG1, GSX2, and Nkx2.1 (FIG. 1E), indicative of a forebrain identity[10,29]. These results suggest that fibroblasts could acquire the mesencephalic regional identity and dopaminergic neural fate through the forced expression of transcription factors Brn2, Sox2, and Foxa2.

TABLE 2

Primer pairs for SYBR-Green-based quantitative Real-Time RT-PCR

| Genes | Forward Primers (5'→3') | Reverse Primers (5'→3') |
|---|---|---|
| Aldh1A1 | GAGTGTGACGTGCTTCCAGA (SEQ ID NO.: 11) | TGGTCCCAGTTGATCATGGC (SEQ ID NO.: 12) |
| Pitx3 | TGCGCTGTCGTTATCGGAC (SEQ ID NO.: 13) | GGTAGCGATTCCTCTGGAAGG (SEQ ID NO.: 14) |

TABLE 2-continued

Primer pairs for SYBR-Green-based quantitative Real-Time RT-PCR

| Genes | Forward Primers (5'→3') | Reverse Primers (5'→3') |
|---|---|---|
| Lmx1α | ACGGCCTGAAGATGGAGGA (SEQ ID NO.: 15) | CAGAAACCTGTCCGAGATGAC (SEQ ID NO.: 16) |
| Nkx6-1 | CTGCACAGTATGGCCGAGATG (SEQ ID NO.: 17) | CCGGGTTATGTGAGCCCAA (SEQ ID NO.: 18) |
| Msx1 | TGCTGCTATGACTTCTTTGCC (SEQ ID NO.: 19) | GCTTCCTGTGATCGGCCAT (SEQ ID NO.: 20) |
| Corin | TGGAGGTGCCTATCAGAGAGA (SEQ ID NO.: 21) | GTGAGATCCAGTAACGCATTCA (SEQ ID NO.: 22) |
| Mash1 | GCAACCGGGTCAAGTTGGT (SEQ ID NO.: 23) | GTCGTTGGAGTAGTTGGGGG (SEQ ID NO.: 24) |
| Ngn2 | GACATTCCCGGACACACACC (SEQ ID NO.: 25) | CTCCTCGTCCTCCTCCTCGT (SEQ ID NO.: 26) |
| Foxg1 | CAAGGCTGACGCACTTGGA (SEQ ID NO.: 27) | CTTGCCGTTCTTCTTGTCGC (SEQ ID NO.: 28) |
| Otx2 | TATCTAAAGCAACCGCCTTACG (SEQ ID NO.: 29) | AAGTCCATACCCGAAGTGGTC (SEQ ID NO.: 30) |
| Gsx2 | CATCATCAAGGACTCCTCACGG (SEQ ID NO.: 31) | GACATCACCAACGGGGACG (SEQ ID NO.: 32) |
| Nkx2-1 | ATGAAGCGCCAGGCTAAGG (SEQ ID NO.: 33) | GGTTTGCCGTCTTTGACTAGG (SEQ ID NO.: 34) |
| GFAP | CTGGAACAGCAAAACAAGGCGCTGG (SEQ ID NO.: 35) | TCCAGCCTCAGGTTGGTTTCATC (SEQ ID NO.: 36) |
| Glast | ACCAAAAGCAACGGAGAAGAG (SEQ ID NO.: 37) | GGCATTCCGAAACAGGTAACTC (SEQ ID NO.: 38) |
| Nestin | CCCTGAAGTCGAGGAGCTG (SEQ ID NO.: 39) | CTGCTGCACCTCTAAGCGA (SEQ ID NO.: 40) |
| Olig1 | TCTTCCACCGCATCCCTTCT (SEQ ID NO.: 41) | CCGAGTAGGGTAGGATAACTTCG (SEQ ID NO.: 42) |
| Olig2 | TCCCCAGAACCCGATGATCTT (SEQ ID NO.: 43) | CGTGGACGAGGACACAGTC (SEQ ID NO.: 44) |
| Ng2 | AGGGGTTCAGCTTTTCGGATT (SEQ ID NO.: 45) | AGTGTTATCATTCTCCGGGGTAG (SEQ ID NO.: 46) |
| S100β | TGGTTGCCCTCATTGATGTCT (SEQ ID NO.: 47) | CCCATCCCCATCTTCGTCC (SEQ ID NO.: 48) |
| Sox1 | GAGATGATCAGCATGTACCTGCC (SEQ ID NO.: 49) | GTAGTGCTGTGGCAGCGAGT (SEQ ID NO.: 50) |
| Pax6 | TGGCAAACAACCTGCCTATG (SEQ ID NO.: 51) | TGCACGAGTATGAGGAGGTCT (SEQ ID NO.: 52) |
| CD133 | TGTTGTTGGCGCAAATGTGG (SEQ ID NO.: 53) | TGTTCCTTGAGCAGATAGGGA (SEQ ID NO.: 54) |
| Sox3 | CAGCTCGAGAGAACGCATCA (SEQ ID NO.: 55) | ACGGGGTTCTTGAGTTCAGT (SEQ ID NO.: 56) |
| Zbtb16 | CTGGGACTTTGTGCGATGTG (SEQ ID NO.: 57) | CGGTGGAAGAGGATCTCAAACA (SEQ ID NO.: 58) |
| L-myc | TTCTACGACTATGACTGCGGA (SEQ ID NO.: 59) | TGATGGAAGCATAATTCCTGCC (SEQ ID NO.: 60) |
| Brn2 (endo) | AGCTGGAGAAGGAGGTGGTGAGAG (SEQ ID NO.: 61) | CACCTGCTACCTGATATAGGATAGTCCAGTG (SEQ ID NO.: 62) |
| Brn2 (tg) | AGCTGGAGAAGGAGGTGGTGAGAG (SEQ ID NO.: 63) | TTTATCGTCGACCACTGTGCTGG (SEQ ID NO.: 64) |

TABLE 2-continued

| Primer pairs for SYBR-Green-based quantitative Real-Time RT-PCR | | |
|---|---|---|
| Genes | Forward Primers (5'→3') | Reverse Primers (5'→3') |
| Sox2 (endo) | CCTCCGGGACATGATCAGCATGTA (SEQ ID NO.: 65) | CGGCATCACGGTTTTTGCGT (SEQ ID NO.: 66) |
| Sox2 (tg) | CCTCCGGGACATGATCAGCATGTA (SEQ ID NO.: 67) | TTTATCGTCGACCACTGTGCTGG (SEQ ID NO.: 68) |
| Foxa2 | TCAACCACCCCTTCTCTATCAACAACC (SEQ ID NO.: 69) | TGGGTAGTGCATGACCTGTTCGTAGG (SEQ ID NO.: 70) |
| Lmx1a (tg) | GATCCCTTCCGACAGGGTCTCAC (SEQ ID NO.: 71) | AGACTGCCTTGGGAAAAGCG (SEQ ID NO.: 72) |
| Fxa2 (tg) | TCAACCACCCCTTCTCTATCAACAACC (SEQ ID NO.: 73) | AGACTGCCTTGGGAAAAGCG (SEQ ID NO.: 74) |

iDPs Expressed Specific Dopaminergic Progenitor Markers and Possess Dopaminergic Neuronal-Restricted Differentiation Potential Ploysialic acid-neural cell adhesion molecule (PSA-NCAM), doublecortin (DCX) and Corin (Lrp4) have been used to identify and isolate neuronal-restricted precursors from ESC-derived neural derivatives[28,30,31]. We characterized the iDPs that we developed through the immunostaining of cells with specific antibodies against PSA-NCAM, DCX and Corin, and observed that the iDPs specifically expressed all three of the marker genes in addition to the NPC marker gene Nestin (FIG. 2A). This suggests that the iDPs are dopaminergic neuron-restricted precursors. We further validated whether the iDPs are dopaminergic neuronal lineage-restricted by differentiating the iDPs into neurons in the presence of SHH and FGF8 stimulation followed by the treatment of BDNF, GDNF and ascorbic acid (AA) for neuronal maturation. Separately, astrocyte and oligodendrocyte differentiation were induced by 10% serum and PDGF/forskolin, respectively. All βIII-tubulin positive neurons derived from iDPs were TH positive (FIG. 2B), suggesting dopaminergic neuronal lineage-restricted fate for the iDPs. In contrast, no GFAP and O4 positive cells were observed after astrocyte and oligodendrocyte differentiation, indicating that the iDPs had committed to the neuronal lineage (FIG. 2C). As a positive control, when WT-NPCs were put in the same astrocyte and oliogodendrocyte differentiation conditions, astrocyte and oliogodendrocyte developed (FIG. 2C). Unlike WT-NPCs, the iDPs also expressed much lower levels of glial-lineage related genes, such as Glast, olig1/2, NG2, GFAP and S100β (FIG. 2D). Since these genes are critical regulators for glial-lineage development, the low expression profile of these genes further validated that the iDPs had given up their glia differentiation potentials and committed to a neuronal fate.

Figure 1:
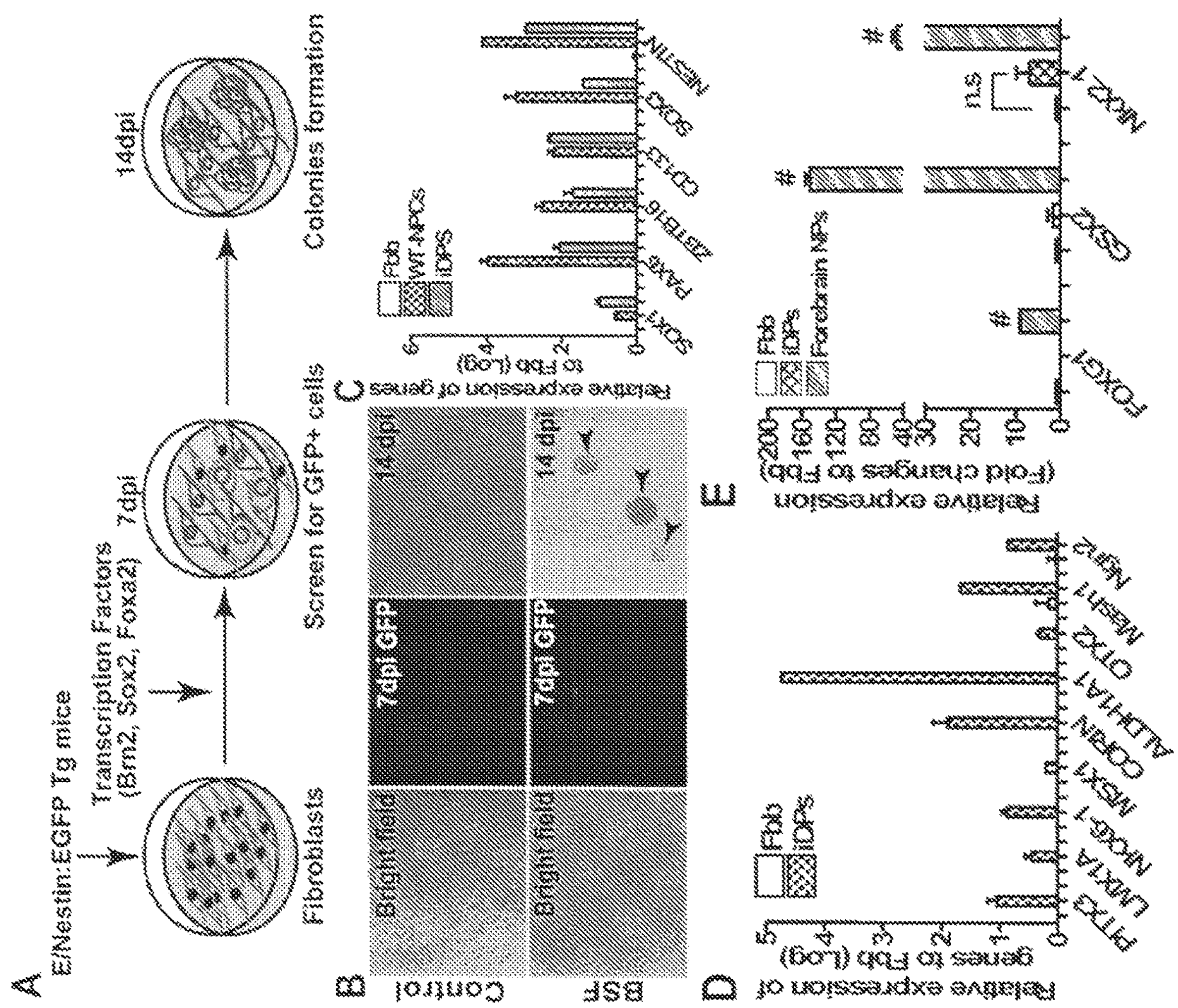
FIGS. 1A-1E. Generation of induced dopaminergic precursors from mouse skin fibroblasts by defined factors Schematic procedure for iDP generation by ectopic overexpression of three transcription factors (Brn2, Sox2 and Foxa2, BSF) (FIG. 1A). Kinetics of iDP generation monitored by GFP occurrence at 7 dpi and clone formation at 14 dpi (indicated by arrows) (FIG. 1B). The expression of a specific set of neural progenitor marker genes (FIG. 1C), ventral mesencephalon (VM) related genes (FIG. 1D), and telencephalon related genes (FIG. 1E) by real-time RT-PCR analysis, and GAPDH-specific primer pairs were used for internal control. Fibroblasts (Fbb) are served as negative control, and primary neural progenitors (WT-NPCs) and forebrain neural progenitors (NPs) served as positive controls. #denotes $p<0.05$ compared to Fbb and iDPs.
Figure 2:
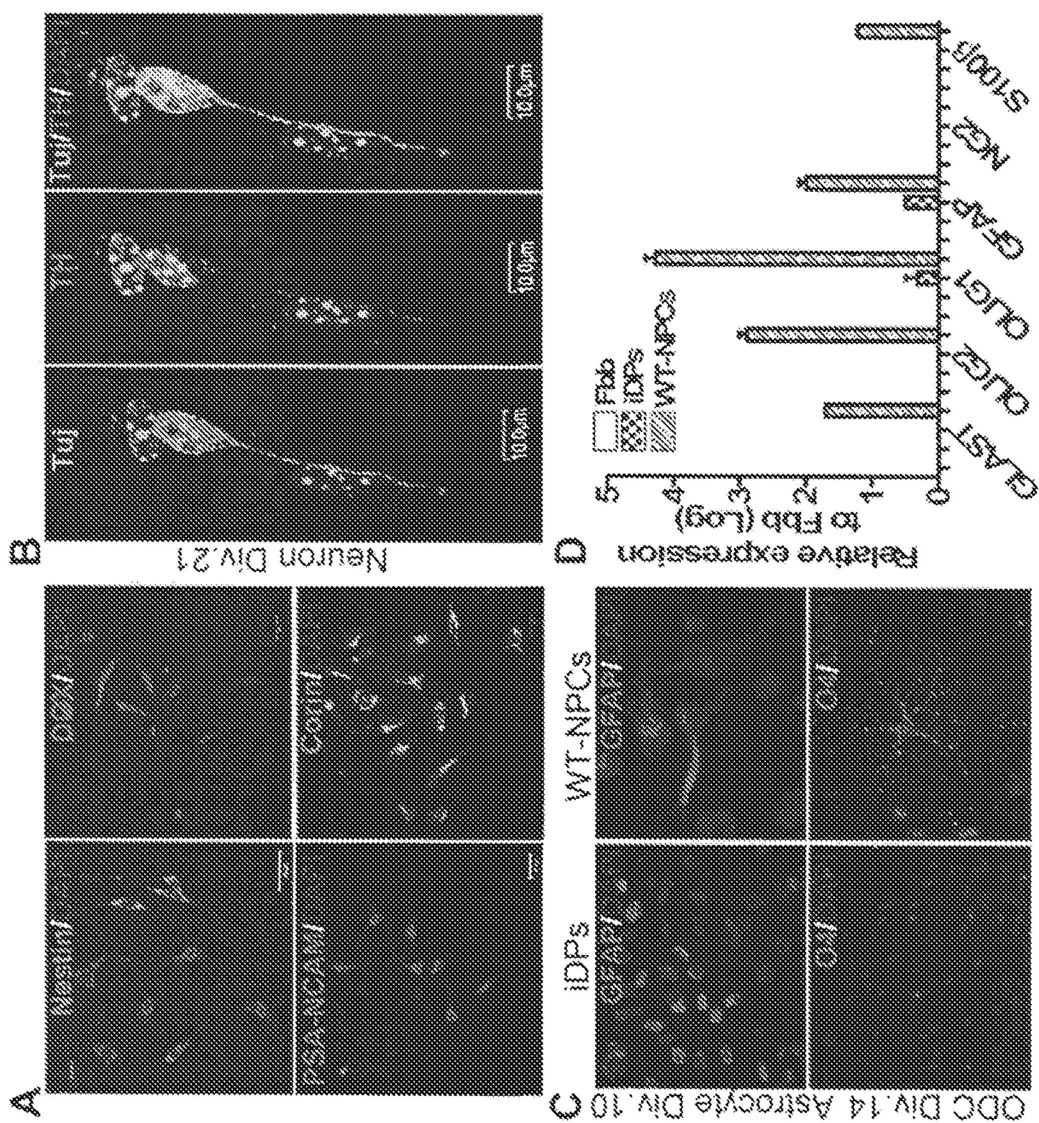
FIGS. 2A-2D. Characterizations of iDPs iDPs cultures were subjected to immunostaining for Nestin (green), Corin (green), DCX and PSA-NCAM (red), and DAPI (blue) (FIG. 2A). iDPs cultured on PLO/laminin-coated coverslips were subjected to dopaminergic neuronal differentiation in the presence of SHH and FGF8, and then immunostaining was performed with antibodies against βIII-Tubulin (green) and Tyrosine hydroxylase (TH, red), and nuclear staining with DAPI (blue) (FIG. 2B). mRNAs were collected from Fbb, WT-NPCs and iDPs, and then subjected to real-time RT-PCR analysis with primers specific for glial-lineage identity (see Table 2), and GAPDH-specific primer pairs were used for internal control (FIG. 2C). WT-NPCs and iDPs cultured on coated coverslips were differentiated with astrocyte medium for 10 days and oligodendrocyte medium for 14 days, respectively, and then subjected to immunostaining with GFAP and O4 (red), and nuclear staining with DAPI (blue) (FIG. 2D). (Scale bars: 20 μm).
Figure 3:
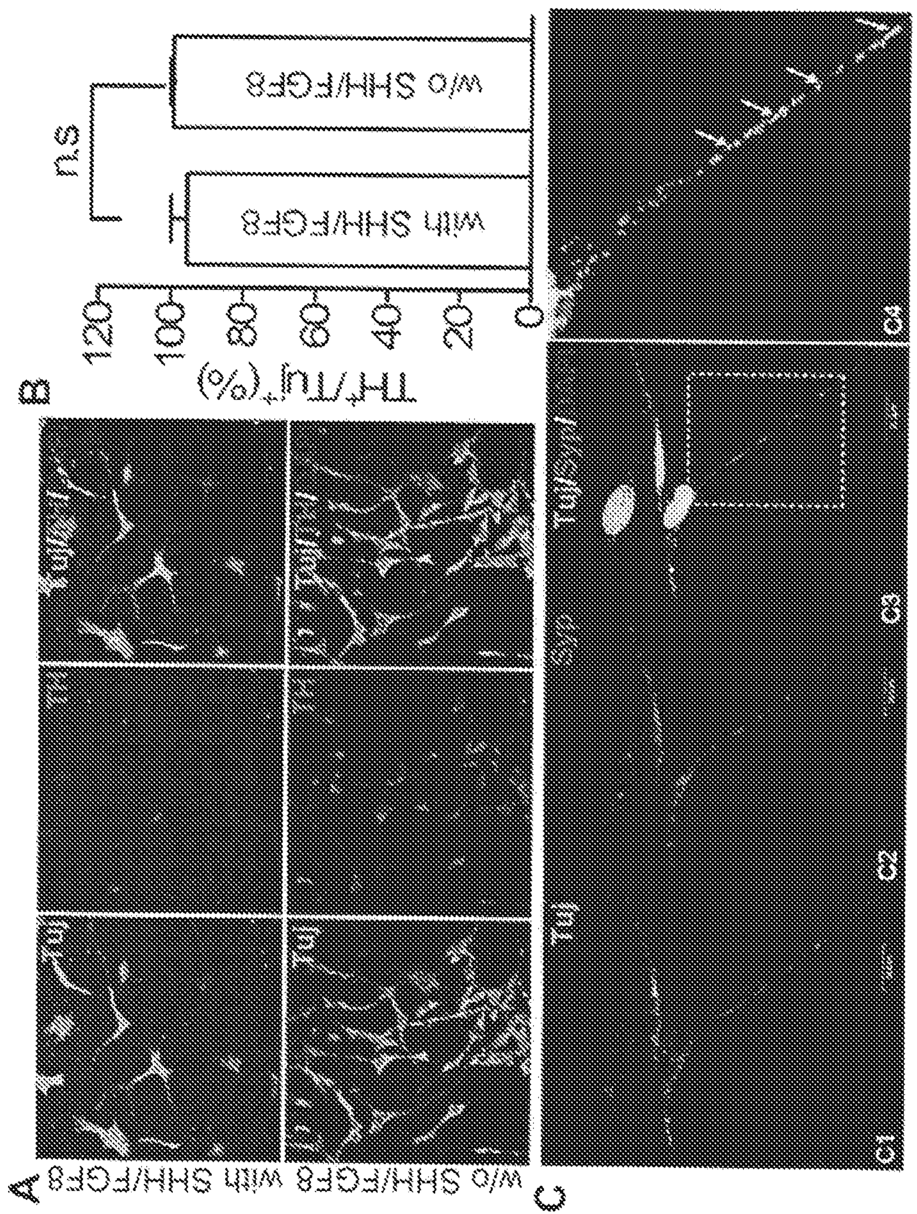
FIGS. 3A-3B. iDPs possess mesencephalic regional identity and differentiate into DA neurons independent of SHH and FGF8 signaling pathway iDPs were treated with SHH and FGF8 for 6 days, and then terminally differentiated in the presence of BDNF, GDNF, IGF1, TGF-β3, dbcAMP and ascorbic acid for another 3 weeks (FIG. 3A, upper panel). Alternatively, iDPs were directly terminally differentiated in the presence of BDNF, GDNF, IGF1, TGF-β3, dbcAMP and ascorbic acid for another 3 weeks (FIG. 3A, lower panel). Cells were fixed and then subjected to immunostaining with βIII-Tubulin (green) and Tyrosine hydroxylase (TH, red), and nuclear staining with DAPI (blue) (FIG. 3A). The percentage of $TH^+$ neurons of total neurons ($Tuj^+$) differentiated from iDPs was shown. No significant difference (n.$) was observed (FIG. 3B). After differentiation, $MAP2^+$ neurons (green) from iDPs were closely associated with presynaptic puncta labeled by synaptophysin (red). Arrows in C4, a large magnification image of box area in C3 shows the presynaptic puncta. (Scale bars: 20 μm)
Figure 4:
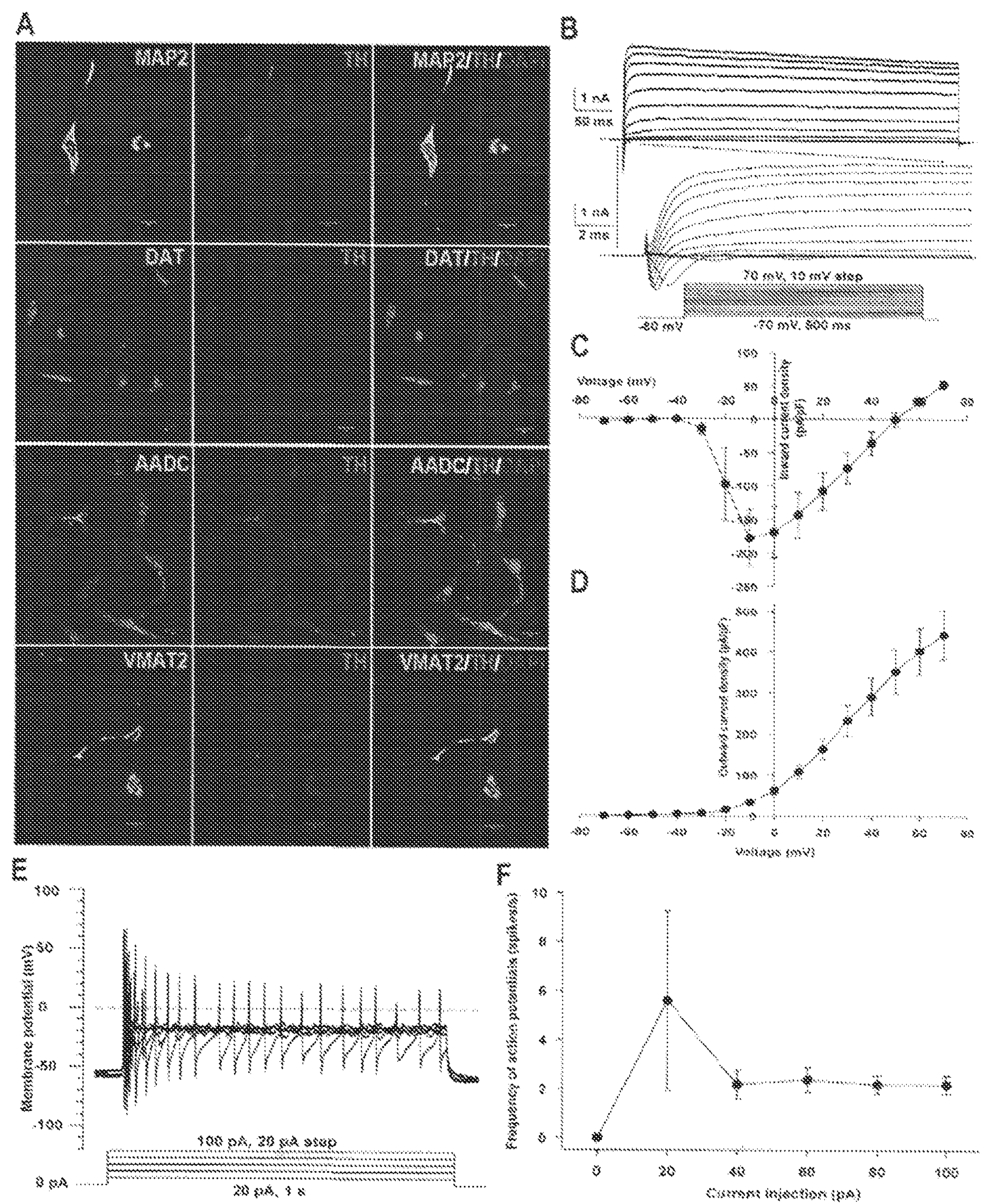
FIGS. 4A-4F. DA neurons derived from iDPs expressed mature neuron markers and exhibited electrophysiological properties iDPs cultured on PLO/laminin-coated coverslips were terminally differentiated in the presence of BDNF, GDNF, IGF1, TGF-β3, dbcAMP and ascorbic acid for 3 weeks, and then subjected to immunostaining with mature DA neuron markers, including MAP2, TH, AADC, DAT and VMAT2 antibodies, and nuclear staining with DAPI (blue) (FIG. 4A). Cells were hyperpolarized to −80 mV for 500 ms before applying depolarizing pulses to elicit inward $Na^+$ and outward $K^+$ currents (FIG. 4B), statistic results showed voltage-dependent inward $Na^+$ and outward $K^+$ currents (FIGS. 4C, 4D). The representative traces of membrane potential changes and action potentials elicited by step-current injections (whole-cell recording, current-clamp mode) generated by DA neurons after 3 weeks of iDP differentiation (FIG. 4E), and statistic result of action potentials was presented in FIG. 4F (n=5). (Scale bars: 20 μm)

Next, the differentiation efficiency of iDPs into dopaminergic neurons was tested. A previously described neuronal differentiation protocol[14] was adopted in the test and it was found that more than 90% of the $Tuj^+$ neurons were $TH^+$ dopaminergic neurons (FIG. 3A). Surprisingly, the efficiency for the iDPs to differentiate into dopaminergic neurons remained high in the absence of the pre-patterning morphogens SHH and FGF8 (FIG. 3B), strongly suggesting the dopaminergic neural fate of iDPs. The iDP-derived neurons also expressed synaptophysin involved in neurotransmitter exocytosis and neuroendocrine[32]. The synaptophysin staining appeared positive in cells of typical neuronal morphology. In contrast, an adjacent cell of different morphology appeared negative for synaptophysin, suggesting a specific staining for synaptophysin (FIG. 3C1-3). Furthermore, the synaptophysin had punctate distribution (FIG. 3C4), indicative of the synaptic formation in vitro. Notably, the iDP-derived DA neurons also exhibited immunoreactivities for aromatic L-amino acid decarboxylase (AADC), the dopamine transporter (DAT) and the brain-specific isoform of the vesicular monoamine transporter (VMAT2) (FIG. 4A), which are three major functionally relevant proteins in dopaminergic neurons. Importantly, the DA neurons derived from iDPs exhibited functional membrane properties of mature neuron. In voltage clamp mode, voltage-gated $K^+$ currents and $Na^+$ currents can be evoked from a holding potential of −80 mV to test potentials range from −70 mV to +70 mV in 10-mV steps (FIGS. 4B, 4C and 4D). In current clamp mode, action potentials can be evoked in all iDPs tested by injection currents from 20 pA to 100 pA in 20-pA steps (FIGS. 4E and 4F, n=5). Those results strongly suggest that iDPs can effectively differentiate and generate mature and functional DA neurons.

Conditional Expression of L-Myc Induced Self-Renewal of iDPs

Figure 5:
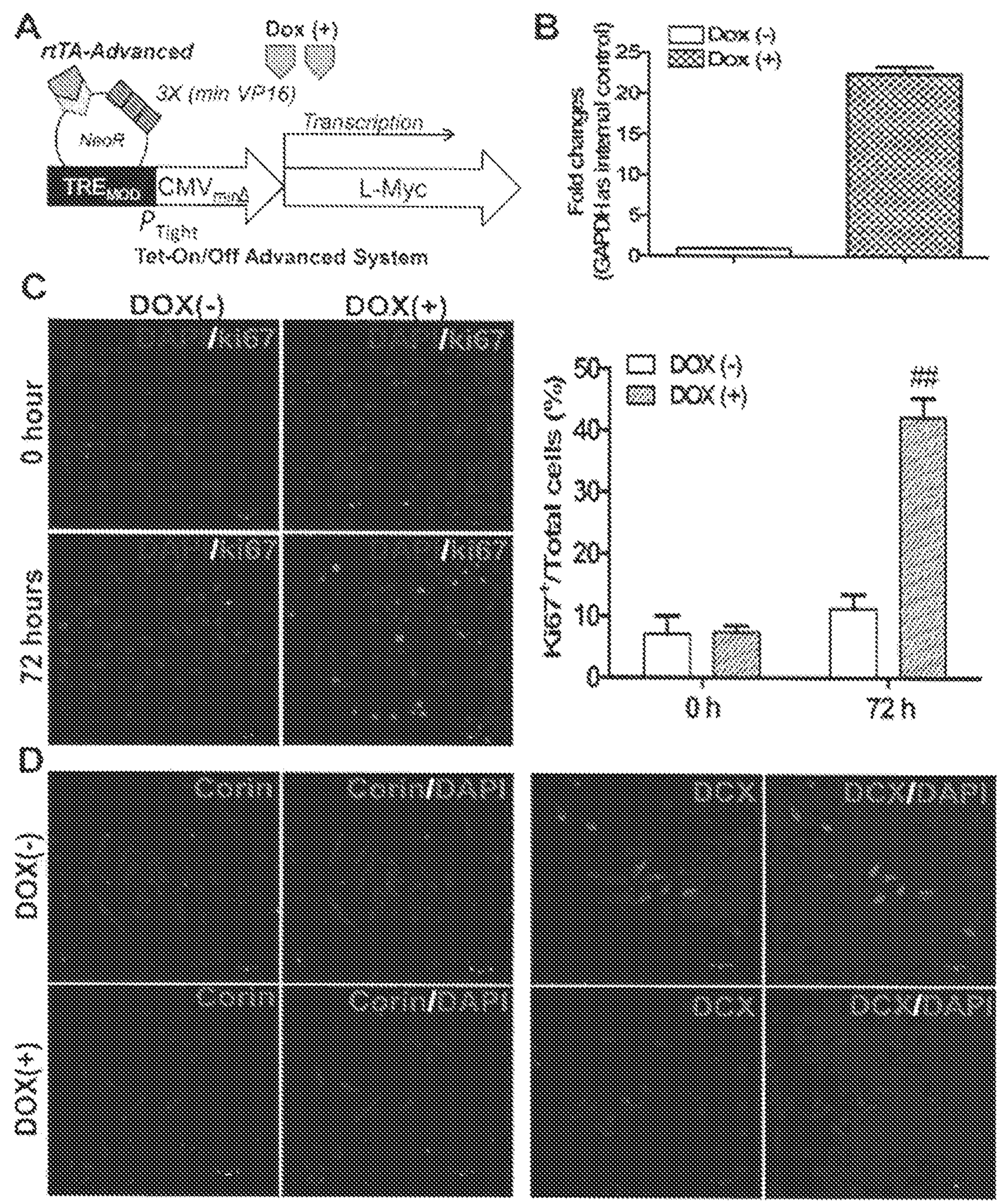
FIGS. 5A-5D. Proliferation and self-renewal of iDPs were enhanced by conditional expression of L-Myc Schematic diagram of Tet-On/Off advanced system for L-Myc overexpression in iDPs (FIG. 5A). Dox-regulated expression of myc (isoform L-myc) in iDPs by real-time RT-PCR analysis with primers specific for L-myc (see Table 2), and GAPDH-specific primer pairs were used for internal control (FIG. 5B). Immunofluorescence staining for Ki67 (red) of cells grown in Dox (+) or Dox (−) media for 72 h, and nuclei were stained with DAPI (blue) (FIG. 5C, left panel). Results are shown as the percentage of $Ki67^+$ cells of total cells (FIG. 5C, right panel). ##denotes $p<0.001$ compared to cells cultured with Dox (−) medium for 72 h. iDPs cultured with Dox (+) or Dox (−) media, respectively, were subjected to immunostaining with Corin and DCX (red) antibodies, and nuclear staining with DAPI (blue) (FIG. 5D). (Scale bars: 20 μm)

During the generation of iDPs, we observed that iDPs exhibited limited ability of self-renewal and clonogenicity, restricting cell expansion required for cell transplantation. We overcame this disadvantage by utilizing a Tet-On/Off system to transduce L-Myc, which is a transformation-deficient, safe and efficient approach that enhances self-renewal[33,34] in iDPs. The conditional expression of L-Myc was under the control of doxycycline (Dox) (FIGS. 5A and 5B). The proportion of Ki67 positive cells significantly increased after DOX treatment for 72 hours (FIG. 5C), whereas the expression levels of DP marker genes Corin and DCX were not affected by the DOX treatment. These results confirmed that using L-Myc to induce self-renewal in iDPs is a safe, effective and efficient strategy for cell expansion intended for cell transplantation.

Figure 6:
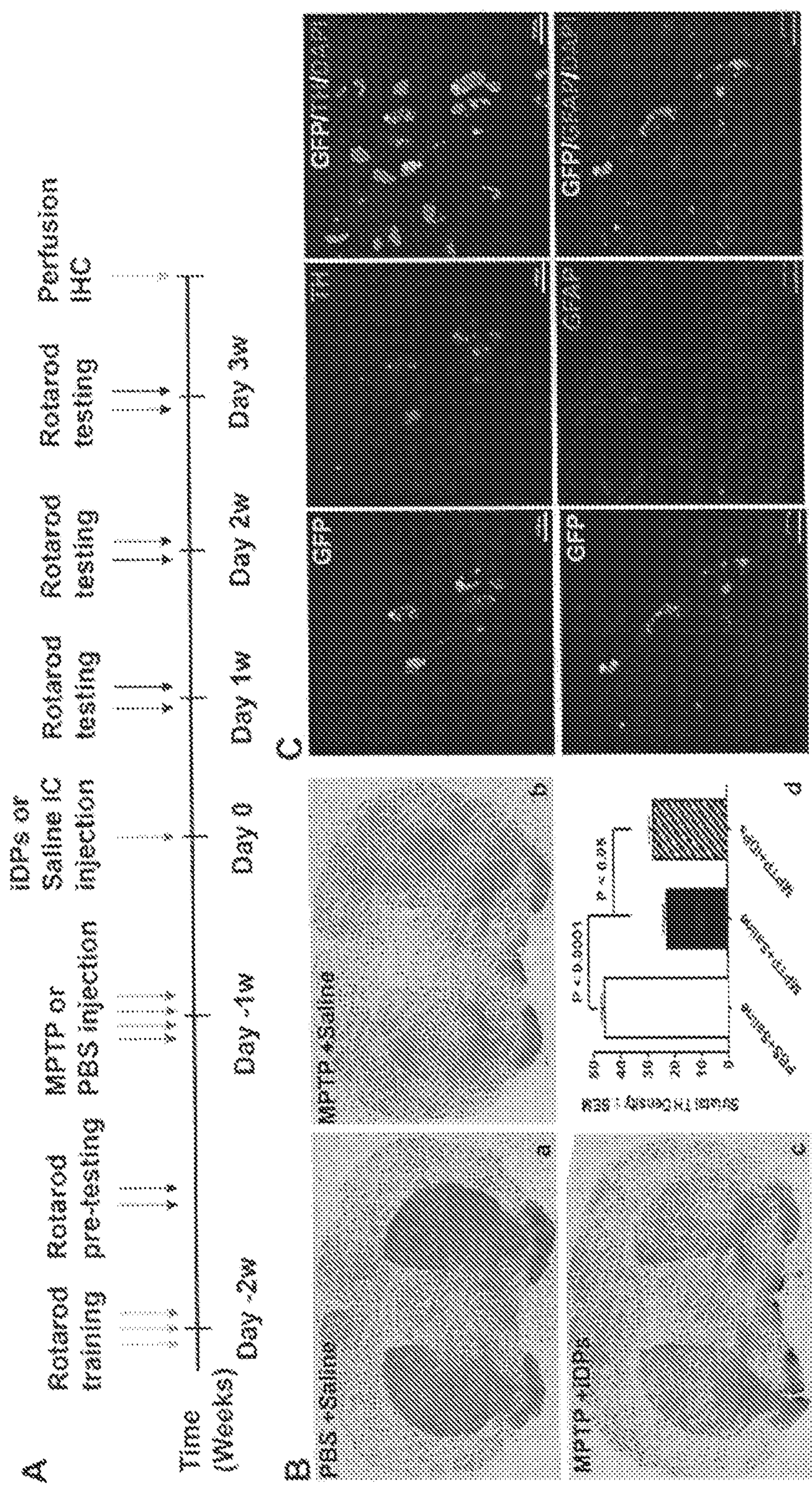
FIGS. 6A-6D. Grafted iDPs survive, differentiate into dopaminergic lineage and partially reverse MPTP striatal pathology FIG. 6A) The training, pretesting, MPTP administration, iDPs inoculation, testing of motor functions, and experimental end point for sacrifice of the mice are shown in the timeline.
Figure 7:
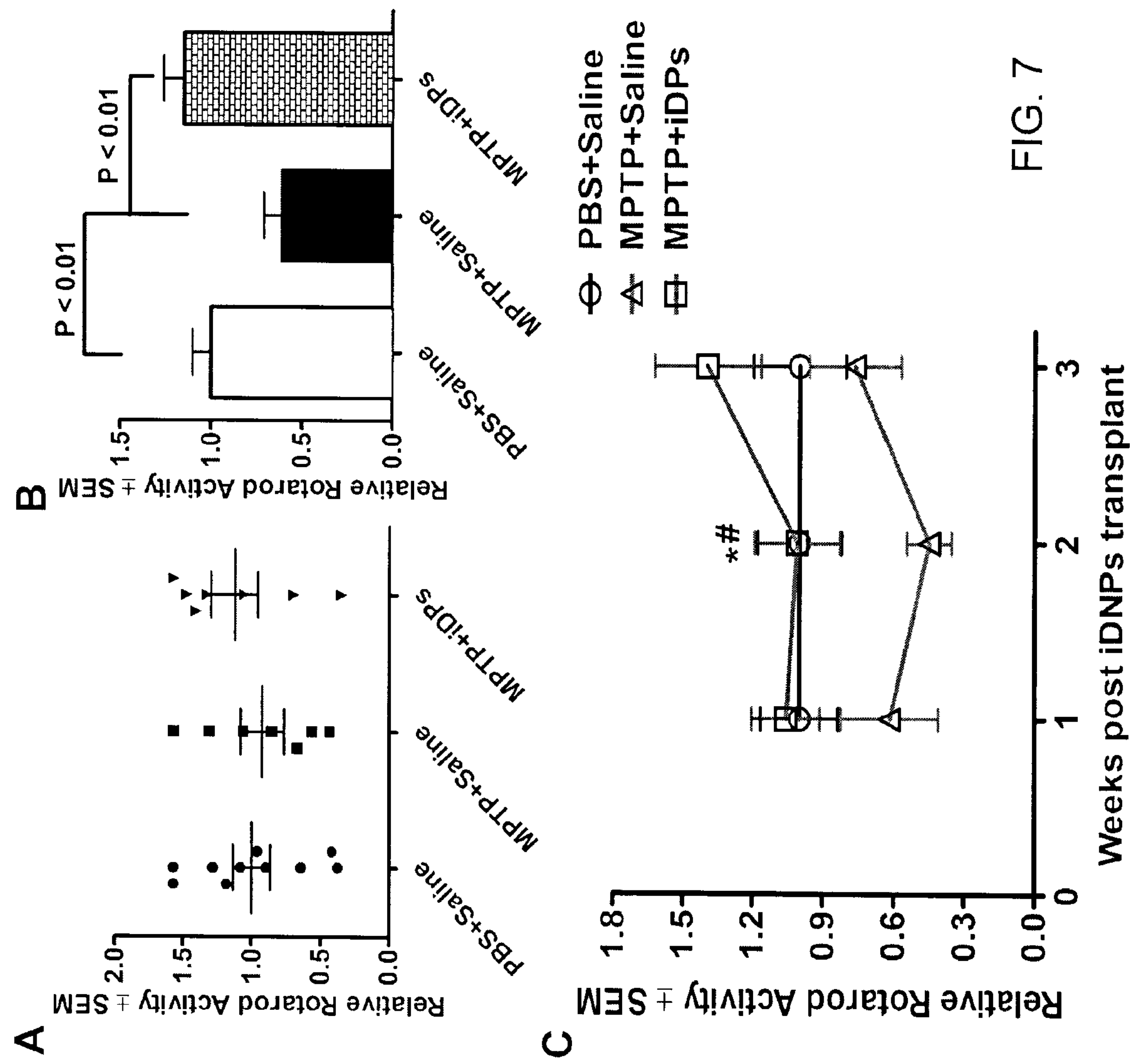
FIGS. 7A-7C. iDPs improve rotarod performance in MPTP-intoxicated mice

Grafted iDPs Survived, Differentiated into Dopaminergic Lineage and Functionally Alleviated Motor Deficits in a MPTP Mouse Model of PD We tested whether the iDPs with conditional L-Myc expression will be safe, and can survive, terminally differentiate into specific dopaminergic neurons in vivo. First, we labeled iDPs with lentiviral vector expressing green fluorescent protein (GFP), and further enriched $GFP^+$ cells by the puromycin resistance in vector (FIG. 11A). $GFP^+$ iDPs were then injected into the striatum of a SCID mouse brain as illustrated in FIG. 11B. At 6 weeks following transplantation, we observed that the grafted GFP+ iDP-derived cells were distributed predominantly around the injection site (FIG. 11C), and the iDP-grafted mice showed no tumor formation at the injection site (FIG. 11D). These results suggest that engineered iDPs are safe for cell transplantation. To evaluate the functionalities of iDPs in vivo, we used a MPTP mouse model of PD as we previously described[35], and performed cell transplantation in PD mouse model as experimental timeline illustrated in FIG. 6A. The mice were trained with rotarod and two trials were performed before MPTP intoxication to establish baseline performance. At one week after MPTP intoxication, iDPs were engrafted on both side of striatum through intracranial (IC) injection. The mice were monitored for 3 weeks for motor functions and then sacrificed for immunohistochemistry. The densities of $TH^+$ DA neuron axonal termini in the striatum were determined by digital image analysis as previously described[36]. The MPTP treatment significantly decreased the densities of $TH^+$ striatal termini, suggesting substantial loss of DA neuronal termini in striatum (FIG. 6B). Densitometric analysis of $TH^+$ striatal termini by week 3 showed 50% loss of $TH^+$ striatal termini. However, engraftment of MPTP mice with iDPs increased striatal termini densities by 20% (40% total loss, FIG. 6B). Interestingly, a majority of the iDP-derived cells were Tuj and TH double positive, but not GFAP positive cells (FIG. 6C), suggesting that the grafted cells survived in vivo for three weeks, and were preferentially differentiated into DA neurons but not astrocytes. Next, we evaluated the effect of iDPs engraftment on motor function of the MPTP mice. All mice group had similar baseline locomotor performance during pre-MPTP testing (FIG. 7A). Rotarod testing of MPTP mice by week 2 showed 55% reduction of locomotor functions. Engraftment of MPTP mice with iDPs increased rotarod performance (FIGS. 7B, 7C). By week 3 (4 weeks after MPTP intoxication), the MPTP mice showed 24% motor deficits compared with PBS group. The iDPs engraftment group had beneficial locomotor effects but not significant recovery of motor deficits (P=0.059, FIG. 7C). Together, these data suggest that iDPs engraftment after the development of MPTP lesion increase motor function in mice.

Human iDP Upon Ectopic Expression of Brn2, Sox2 and Foxa2

Brn2, Sox2 and Foxa2 in fibroblast cells obtained from a PD patient and a 105d fetus were then ectopically expressed and transdifferentiated into iDPs according to the same protocol as mouse cells. The transdifferentiated cells also showed iDP phenotypes such as Corin and DCX expression and colocalization (FIGS. 12A-12B). Significantly, this suggested that autologous iDPs can be prepared from patients of Parkinson's disease (PD), and then be used in in vitro study and/or cell replacement therapy in vivo.

DISCUSSION

Stem cell-based therapy holds a promising future for the treatment of neurodegenerative disorders, particularly in the case of PD. To achieve cell-based therapy for PD, significant efforts have been made to differentiate human embryonic stem cells (ESCs) and induced pluripotent stem cells (iPSCs) to midbrain DA neurons following morphogenic stimulation[37-40]. Recently, direct conversion of cells of one lineage into another has served as an alternative strategy for engraftable cell sources. As a result, induced DA neurons[7,41] and induced neural stem/progenitor cells (iNPCs)[10-13] were generated and showed promise for DA neuron generation. However, the differentiation efficiency, safety, and the specificity of these cells remain a challenge. In the present study, we reported a novel cocktail of three transcription factors (Brn2/Brn4, Sox2 and Foxa2/Lmx1a) that successfully converted mouse skin fibroblasts into neural progenitors. The resulting iDPs were dopaminergic neuronal-restricted and independent of the pre-patterning by SHH/FGF8 (FIGS. 1-3). Most importantly, DA neurons derived from iDPs expressed the mature DA neuron markers in vitro, exhibited electrophysiological properties of mature DA neurons (FIG. 4), and survived in vivo for 6 weeks without tumor formation (FIG. 11), suggesting the iDPs can serve as a safe and efficient cell source for PD treatment.

Previous studies have employed Brn2/Brn4 and Sox2 as neural fate determinants for direct reprogramming of neural progenitor cells from fibroblasts[10,13,17,19], but additional factors may be required to achieve the regional specification and neuronal-lineage restriction[10,19]. Foxa2 and Lmx1a appear to be critical factors that support the regulatory networks required for midbrain DA specification and the transcriptional control of midbrain dopaminergic development. To selectively generate the dopaminergic precursors, we decided to express Foxa2 and Lmx1a in 5F-iNPCs previously developed by our laboratory. The expression of Foxa2 and Lmx1a endowed 5F-iNPCs with midbrain identity and dramatically increased the yield of $TH^+$ neurons (FIG. 8, FIG. 9), suggesting that these two factors could be used to improve the iNPCs-based cell therapy in PD.

Foxa2 and Lmx1a/b are known to cooperatively regulate the proliferation, specification, and differentiation of midbrain dopaminergic progenitors. More specifically, Foxa2 and Lmx1a/b are key transcription factors downstream of strong morphogens (SHH and Wnt1, respectively) that synergistically control the midbrain dopaminergic differentiation by forming two regulatory loops[23,42]. Previous studies on Foxa1/2 predominantly concentrated on the specification of midbrain progenitor identity and their regulatory roles on Lmx1a/b and Helt[26,43-45]. Foxa2 expression is restricted to the mesencephalic floor plate where it plays both SHH-dependent and -independent roles in the specification of floor plate from which DA neurons originate[25,46]. However, it is unclear whether Foxa2 may be a more potent determinant of midbrain DA progenitors than Lmx1a and SHH, or whether Foxa2 could serve as a reprogramming factor favoring the generation of DA neurons. In contrast, given the synergistic control by Foxa2 and Lmx1a/b of the midbrain dopaminergic differentiation, it is unlikely that either is sufficient by itself.

In this study, we have tested novel sets of transcription factors that included Brn2 and Sox2 with one or both of Foxa2 and Lmx1a in the reprogramming of fibroblasts as illustrated in the procedure (FIG. 1A). We observed that all combinations resulted in the clonogenicity at 14 day post-infection (data not shown). Thus, either the combination of Brn2, Sox2 and Foxa2, or the combination of Brn2, Sox2 and Lmx1a can be used to transdifferentiate fibroblasts. Furthermore, the combination of Brn2, Sox2 and Foxa2 successfully converted fibroblasts into stable and expansible iDPs. The iDPs expressed the specific neural progenitor markers, and also exhibited the midbrain identity characterized by the marker genes for dopaminergic neural progenitor cells, such as Aldh1A1, Corin (Lrp4), Lmx1a, Msx1, Ngn2, Otx2, Mash1, Pitx3 and Nkx6.1 (FIG. 1). Among these markers, Aldh1A1 and Corin have been used to specifically mark DPs in the brain and isolate DPs from ES cell-derivatives[28,47]. In addition, DCX and PSA-NCAM have been used to isolate the neuronal lineage-restricted progenitors[24,30,31]. Otx2 prevents the serotonin fate of the progenitors by repressing Nkx2.2[48], and Foxa2 negatively regulates Helt to inhibit the GABAergic neuron differentiation in the ventral midbrain[43-45]. Because the reprogramming factors Brn2 and Sox2 could not generate DA-specified iNPCs, our results suggest that Foxa2 can work cooperatively with Brn2 and Sox2 to drive the direct conversion of fibroblasts into iNPCs with midbrain progenitor identity.

It should be noted that given Brn2 and Brn4 have previously been used interchangeably in several transdifferentiation studies, here a Brn4, Sox2 and Foxa2 combination (or Brn4, Sox2 and Lmx1a; or Brn2, Brn4, Sox2 and Foxa2; or Brn2, Brn4, Sox2 and Lmx1a; or Brn2, Brn4, Sox2, Foxa2 and Lmx1a) can also be used to transdifferentiate fibroblasts.

Our present study demonstrates that ectopic expression of Foxa2 positively regulates Lmx1a, Otx2 and other key transcription factors responsible for DA neuron development, and negatively regulates transcription factors related to glial cell development (FIG. 2). Thus, the resulting iDPs are committed to the dopaminergic lineage with minimum glial cells differentiation potential (FIG. 2). Terminal differentiation in the presence of BDNF, GDNF and AA could steer the iDPs into mature and functional DA neurons independent of SHH/FGF8 stimulation (FIG. 3 and FIG. 4). This role of Foxa2 is consistent with a previous report that shows Foxa2 can execute the midbrain floor plate program via SHH-independent and -dependent mechanisms[46].

In vivo grafted NSCs/NPCs often terminally differentiate into astrocytes rather than functional neurons in response to injury[15,16]. Our strategy in engineering iDPs with controllable L-Myc expression (FIG. 5) is a confirmation of the way to efficiently, safely and practically control the self-renewal of iDPs[33,34]. When the iDPs were transplanted into the striatum of MPTP PD mouse model following the timeline illustrated in FIG. 6A, we observed that MPTP injection damaged $TH^+$ neurons in the striatum, whereas grafted iDPs significantly recovered the striatal TH density after cell transplantation, and very few of them terminally differentiated into astrocytes. Indeed, the majority of cells differentiated into DA neurons at 6 weeks post-transplantation, and no tumor or cell outgrowths were observed, and the partially recovery of motor function in PD mouse model after cell transplantation further suggest that the iDPs may serve as a useful cell source for PD treatment.

Collectively, we demonstrated that Brn2/Brn4, Sox2 and Foxa2/Lmx1a could successfully convert mouse skin fibroblasts into induced neural progenitors, and Foxa2/Lmx1a confers the induced neural progenitors with the specification of midbrain identity and DA lineage. The success of this work could also provide an important foundation for a cellular model to investigate the pathogenesis of PD when patient skin fibroblasts are reprogrammed into iDPs with Brn2/Brn4, Sox2 and Foxa2/Lmx1a in vitro. Finally, the managed expansion of the engineered iDPs further provides a promising therapeutic cell source for PD.

Methods

Cell Preparation, Retroviral Packaging, Infection and Direct Reprogramming

Mouse skin fibroblasts were isolated from adult Nestin-EGFP transgenic mice (kindly provided by Richard J Miller from Northwestern University, Chicago, Ill.) aged 5.5-7.0 weeks as previously described[13], with approval of the University of Nebraska Medical Center Institutional Animal Care and Use Committee and following National Institutes of Health (NIH) ethical guidelines. Fibroblasts were cultured in Dulbecco's modified Eagle's medium supplemented with 10% FBS, 1×Non-Essential Amino Acid, 100 U/mL penicillin, 100 μg/mL streptomycin at 37° C. in a 5% $CO_2$ humidified atmosphere. Fibroblasts were used within passage 2-5 to avoid replicative senescence. Mouse Brn2 ORF (EcoRI+Not I), Foxa2 ORF (BamHI+Xho I) were cloned into pMXs-retroviral vectors (Cellbiolabs, RTV-010), and pMXs-Sox2 was purchased from Addgene (Plasmid #13367). Retroviruses (pMXs) were generated with Plat-E packaging cells as previously described[49]. In brief, Plat-E cells were seeded at $3.6\times10^6$ cells per 100-mm dish. 24 hours after seeding, 15 μg DNA of pMXs-based retroviral vectors encoding Sox2, Brn2 and Foxa2 were introduced into Plat-E cells using 15 μL of Lipofectamine™ LTX transfection reagent (Invitrogen). The medium was replaced with 5 mL of DMEM containing 5% FBS 24 hours after transfection. Fibroblasts from Nestin-EGFP transgenic mice were seeded at $2\times10^5$ cells per 35-mm dish. At 48-hour and 72-hour post-transfection, virus-containing supernatants from these Plat-E cultures were recovered and filtered through a 0.45-μm cellulose acetate filter. Equal volumes of the supernatants were mixed and supplemented with 10 μg/mL polybrene. Cells were incubated in virus/polybrene-containing supernatants overnight. The medium was changed 3 days after infection to NeuroCult® NSC Basal (Stem Cell Technologies, Inc., Vancouver, BC V5Z 1B3, Canada) Medium supplemented with NeuroCult® NSC Proliferation Supplements (Stem Cell Technologies, Inc.), 20 ng/mL basic fibroblast growth factor (bFGF, BioWalkersville), and 20 ng/mL epidermal growth factor (EGF, BioWalkersville). After 9-14 days, the predicted iDP colonies were monitored by fluorescence microscope.

Quantitative Real-Time RT-PCR

Total mRNA was isolated with TRIzol Reagent (Invitrogen) and RNeasy Mini Kit (QIAGEN Inc., Valencia, Calif.) using the manufacturer's recommendations. The reverse transcription was performed using Transcription $1^{st}$ Strand cDNA Synthesis Kit (Roche, USA). The RT-PCR analyses for the detection of neural stem cell-specific mRNAs were performed using SYBR® Select Master Mix (Life Technologies, Los Angeles, Calif.) with 0.5 μL of cDNA, corresponding to 1 μg of total RNA in a 15 μL final volume, 1.5 μL $H_2O$, 7.5 μL SYBR Green, 5.5 μL oligonucleotide primer pairs (synthesized at Fisher) at 1 mM (See Table 2). PCR program: 1. 50° C. for 2 min, 2. 95° C. for 2 min; 3. 95° C. for 15 sec, 4. specific annealing temperature for 15 sec, 5. 72° C. for 1 min. Steps 2-4 were repeated 40 times. All samples were amplified in triplicate and the mean was used for further analysis.

Immunocytochemistry

The cultured cells were fixed in 4% formaldehyde for 20 min at room temperature and then washed with PBS for three times. The fixed cells were permeabilized with 0.2% Triton X-100 in PBS for 10 min, and blocked with 2% BSA in PBS for 1 hour at room temperature. Cells were incubated with primary antibodies as listed in Table 2 overnight, and then washed with PBS for three times and incubated for 2 hours at room temperature with secondary antibodies (See Table 3). Fluorescent images were obtained using a Zeiss 710 Confocal Laser Scanning Microscope (Carl Zeiss, Oberkochen, Germany).

Differentiation

For astrocyte differentiation, the iDP culture medium was replaced by DMEM/F-12 with 10% FBS, and cultured for 7 days, with the medium changed every other day. For oligodendrocyte differentiation, iDPs were cultivated in DMEM/F12 with 1×N2, 10 ng/mL PDGF (R&D Systems, Minneapolis, Minn.), 10 ng/mL FGF-2 and 10 μM forskolin (Sigma-Aldrich, Saint Louis, Mo.) for 4 days. Afterwards, PDGF and forskolin were replaced by 30 ng/mL 3, 3, 5-triiodothyronine (T3) hormone and 200 mM ascorbic acid (all from Sigma-Aldrich, Saint Louis, Mo.) for another 7 days. For neuronal differentiation, SHH/FGF8 independent protocol:iDPs were plated on poly-L-Ornithine/laminin-coated coverslips in 24-well plate with DMEM/F12 supplemented with 1×N2, 1×B27, 1.0 mM Glutamax, 0.11 mM β-mercaptoethanol, 1.0 mM dibutyrylcAMP (Sigma), 0.2 mM ascorbic acid (Sigma), 10 ng/mL brain-derived neurotrophic factor (BDNF) (Peprotech), and 10 ng/mL glial cell line-derived neurotrophic factor (GDNF) (Peprotech) for 4 weeks. The medium was changed every 3-4 days. Unless otherwise indicated, all reagents were purchased from Invitrogen (Carlsbad, Calif., USA); SHH/FGF8 dependent protocol: Cells were plated on poly-L-Ornithine/laminin-coated coverslips in 24-well plate with DMEM/F12 containing with 1×N2, 10 ng/mL bFGF (Peprotech), 100 ng/mL SHH (Peprotech), 100 ng/mL FGF8 (Peprotech) for 6 days, and then switched to DMEM/F12 containing 1×N2, 1×B27, 1.0 mM Glutamax, 0.11 mM β-mercaptoethanol, 1.0 mM dibutyrylcAMP (Sigma), 0.2 mM ascorbic acid (Sigma), 10 ng/mL brain-derived neurotrophic factor (BDNF) (Peprotech), and 10 ng/mL glial cell line-derived neurotrophic factor (GDNF) (Peprotech) for another 4 weeks, and the medium was changed every 3-4 days.

Retroviral Infection, Isolation, and Expansion of iDPs

L-Myc was cloned into the Tet-All retroviral-vector, which contained both reverse tetracycline-controlled transactivator (rtTA) and tetracycline response element (TRE) promoter. The original backbones for the Tet-All vector were pRetroX-Tight and pRetro-rtAT-Advanced from Clontech Laboratories (Mountain View, Calif., USA). The retrovirus encoding L-Myc was packaged in Plat-E cells, and iDPs were infected with the virus and screened with neomycin (neo).

Recording of Action Potentials and Total Currents

Action potentials and total currents were recorded by the whole cell patch-clamp technique using Axonpatch 200B patch-clamp amplifier (Axon Instruments, Sunnyvale, Calif.). pClamp 10.2 program was used for data acquisition. The patch-pipette solution was composed of (in mM): 105 K-aspartate, 20 KCl, 1 $CaCl_2$, 5 MgATP, 10 HEPES, 10 EGTA, and 25 Glucose (pH 7.2; 320 mOsm/L). The bath solution consisted of (in mM): 140 NaCl, 5.4 KCl, 0.5 $MgCl_2$, 2.5 $CaCl_2$, 5.5 HEPES, 11 Glucose, and 10 Sucrose (pH 7.4; 330 mOsm/L). The same pipette and bath solutions were used for action potentials and total currents measurement. Resistance of the patch pipette was 3-5 MΩ. Series resistance of 6-13 MΩ was electronically compensated 80-90%. Action potentials were elicited by a series of 1-s depolarizing currents injection from 20 pA to 100 pA with 20-pA increments. Total currents were evoked from a holding potential of −80 mV by stepping to voltages between −70 and +70 mV in 10 mV increment for 500 ms. Recorded traces were sampled at 10 kHz and filtered at 5 kHz. All experiments were done at room temperature.

MPTP Intoxication and iDPs Engraftment

Adult male 8-week-old C57BL/6J mice were purchased from Jackson Laboratories (Bar Harbor, Me.) and housed on a 12:12 hour light/dark cycle with ad libitum access to food and water in the animal facilities at the University of Nebraska Medical Center. All animal procedures were conducted according to protocols approved by the Institutional Animal Care and Use Committee at the University of Nebraska Medical Center. Mice were randomly assigned to treatment groups before motor function and behavior training (FIG. 6A). MPTP intoxication was performed as previously described[35]. Briefly, mice received four subcutaneous injections, one every 2 hours of either vehicle (phosphate buffered saline (PBS) at 10 ml/kg) or MPTP-HCL (20 mg/kg, free base in PBS; Sigma-Aldrich Co, St. Louis, Mo., USA). MPTP handling and safety measures were in accordance with the published guidelines[50]. For iDPs engraftment, at 7 days after MPTP intoxication, mice were anesthetized with Ketamine (120 mg/kg) and xylazine (16 mg/kg) by i.p, placed in a stereotaxic apparatus (Stoelting, Wood Dale, Ill., www.stoeltingco.com) for IC injection (FIG. 6A). A linear skin incision was made over the bregma, and two 1-mm burr holes were drilled in the skull 0.2 mm posterior and 3.5 mm lateral to the bregma using a hand-held driller. iDPs (0.25 million per injection) were labeled with GFP expressing retrovirus and injected into the striatum of both hemispheres. Saline was used as a control for iDPs injection. Coordinates for inoculation were set as: 0.22 mm posterior to bregma, 3.25 mm lateral from the Sagittal midline, and a depth of 2.9 mm in vertical line. A Hamilton 10-μl syringe (Fisher) was used for cell injection. Mice were sacrificed 21 days post-injection after intracardiac perfusion and brains were quickly removed. Immunohistochemistry for $TH^+$ nerve terminals and quantification were performed in a blinded fashion as previously described[35,51].

Motor Function and Behavior Tests

Rotarod test was used to evaluate the recovery of MPTP-induced motor deficits by the engrafted iDPs. The apparatus was fitted with a 7-cm diameter rod and was interfaced with automatic timing instrumentation (Rotamex, Columbus Instruments, Inc., Columbus, Ohio, USA). Mice were habituated and trained to perform on the accelerating rotarod at 2-12 rpm for 5 min for four daily sessions in three consecutive days prior to the administration of MPTP. Twice before MPTP-intoxication, all mice were evaluated at 10 rpm for a maximum of 90 s per trial to obtain a pre-treatment baseline performance. After iDPs engraftment, mice were re-evaluated on the rotarod twice a week for 3 weeks. Weekly post-treatment rotarod performance was calculated as average of two trials and as a ratio relative to animal group's baseline performance. Scores from MPTP mice with or without iDPs engraftment were normalized to the mean performance of the PBS control group[35,51].

Statistical Analysis

Data were expressed as means±SD and statistically evaluated by analysis of variance (ANOVA) followed by the Tukey's test for paired observations unless specified. Significance was considered as a p value of $<0.05$. All assays were performed at least twice, with triplicate samples in each experiment.

Cell Labeling, Transplantation and Histology iDPs with controllable L-Myc (Tet-On/Off advanced system) were transduced by lentiviruses packaged by pLenti-CMV-GFP-Puro with psPAX2 and pMD2.G (Addgene) in 293T cells using Lipofectamine® LTX Reagent with PLUS™ Reagent (Invitrogen™). Titers of lentiviral preparations were determined using 293T cells and ranged between $10^7$-$10^8$ IFU/ml. iDPs were expanded in NeuroCult® NSC basal medium supplemented with NeuroCult® NSC Proliferation supplements (Stem Cell Technologies, Inc.), 20 ng/mL bFGF (BioWalkersville), and 20 ng/mL EGF (BioWalkersville) and screened by adding Dox (4 μg/ml) and G418 (400 ng/ml). Four-week-old male C.B.-17 SCID mice were purchased from the Charles River Laboratory. All mice were housed in the animal facilities at the University of Nebraska Medical Center. All procedures were conducted according to protocols approved by the Institutional Animal Care and Use Committee (IACUC) of the University of Nebraska Medical Center. Briefly, mice were anesthetized with Ketamine (120 mg/kg) and xylazine (16 mg/kg) by i.p, placed in a stereotaxic apparatus (Stoetling, Wood Dale, Ill.) for intracranial injection in the left cerebral hemisphere. GFP-expressing iDPs ($0.5\times10^6$/5 μL) were injected with a 10-μl syringe into the striatum of mouse brain. Coordinates for inoculation were set as: 0.5-0.8 mm posterior to bregma, 3.5 mm lateral form the sagittal midline, a depth and angle of 3.6 mm and 35° from the vertical line. Mice were anesthetized and perfused with 4% paraformaldehyde (PFA) 6 weeks after injection, and brains were immediately removed and then placed in 4% PFA for postfixation overnight. After dehydration in 30% sucrose solution, brains were frozen and cut on a cryostat (30 μm), and sections were then scanned using a Leica Confocal Microscope and Metamorph analysis software (Molecular Devices). In addition, fixed brains were embedded in paraffin, and sections were stained with hematoxylin and eosin (H&E), and images were acquired and analyzed by Ventana's Coreo Au Slider Scanner.

TABLE 3

1st and 2nd antibodies used for immunofluorescence

| 1st Antibody | Isotype | Dilution | Source |
|---|---|---|---|
| GFAP | Rabbit Ig G | 1:1,000 | DAKO |
| MAP2 | Mouse Ig G | 1:1,000 | Sigma |
| MAP2 | Rabbit Ig G | 1:1,000 | Millipore |
| Nestin (10C2) | Mouse Ig G | 1:1,000 | ThermoFisher |
| O4 | Mouse Ig G | 1:1,000 | R&D Systems |
| Synaptophysin | Rabbit Ig G | 1:1,000 | abcam |
| Msx GFP | Mouse Ig G | 1:800 | Millipore |
| Anti-Tyrosine Hydroxylase (TH) | Sheep Ig G | 1:2,000 | Jackson ImmunoResearch |
| Anti-Tyrosine Hydroxylase (TH) | Rabbit Ig G | 1:1,000 | Calbiochem ® |
| βIII-Tubulin | Mouse Ig G | 1:1,500 | Sigma |
| βIII-Tubulin | Rabbit Ig G | 1:1,500 | Sigma |
| DOPA Decarboxylase | Rabbit Ig G | 1:500 | abcam |
| DAT | Rabbit Ig G | 1:1,000 | Biocompare |
| VMAT2 (9E11) | Mouse Ig G1 | 1:100 | NOVUS Biologicals |
| Ki67 | Rabbit Ig G | 1:1,000 | abcam |
| Corin (Lrp4) | Rabbit Ig G | 1:1,000 | R&D Systems |
| Doublecortin (DCX) | Goat Ig G | 1:1,000 | Santa Cruz Biotechnology |
| PSA-NCAM | Rabbit Ig G | 1:1,000 | Millipore |
| **2nd Antibodies** | **Isotype** | **Dilution** | **Source** |
| Alexa Fluor ® 488 | Goat anti-Rabbit Ig G | 1:1,000 | Molecular Probes |
| | Goat anti-Mouse Ig G | 1:1,000 | Molecular Probes |
| | Rabbit anti-Goat Ig G | 1:1,000 | Molecular Probes |
| | Rabbit anti-Mouse Ig G | 1:1,000 | Molecular Probes |
| | Donkey anti-goat Ig G | 1:1,000 | Molecular Probes |
| | Donkey anti-Sheep Ig G | 1:1,000 | Jackson ImmunoResearch |
| Alexa Fluor ® 594 | Goat anti-Rabbit Ig G | 1:1,000 | Molecular Probes |
| | Donkey anti-goat Ig G | 1:1,000 | Molecular Probes |
| | Donkey anti-Rabbit Ig G | 1:1,000 | Molecular Probes |
| | Donkey anti-Sheep Ig G | 1:1,000 | Jackson ImmunoResearch |
| Alexa Fluor ® 568 | Goat anti-Mouse Ig G | 1:1,000 | Molecular Probes |
| Alexa Fluor ® 647 | Donkey anti-Rabbit Ig G | 1:1,000 | Molecular Probes |

REFERENCES

1 Dauer, W. & Przedborski, S. Parkinson's disease: mechanisms and models. *Neuron* 39, 889-909 (2003).

2 Lindvall, O. & Kokaia, Z. Stem cells in human neurodegenerative disorders—time for clinical translation? *J Clin Invest* 120, 29-40 (2010).

3 Takahashi, K. & Yamanaka, S. Induction of pluripotent stem cells from mouse embryonic and adult fibroblast cultures by defined factors. *Cell* 126, 663-676 (2006).

4 Yu, J. et al. Induced pluripotent stem cell lines derived from human somatic cells. *Science* 318, 1917-1920 (2007).

5 Vierbuchen, T. et al. Direct conversion of fibroblasts to functional neurons by defined factors. *Nature* 463, 1035-1041 (2010).

6 Ambasudhan, R. et al. Direct reprogramming of adult human fibroblasts to functional neurons under defined conditions. *Cell Stem Cell* 9, 113-118 (2011).

7 Caiazzo, M. et al. Direct generation of functional dopaminergic neurons from mouse and human fibroblasts. *Nature* 476, 224-227 (2011).

8 Kim, J. et al. Functional integration of dopaminergic neurons directly converted from mouse fibroblasts. *Cell Stem Cell* 9, 413-419 (2011).

9 Liu, X. et al. Direct reprogramming of human fibroblasts into dopaminergic neuron-like cells. *Cell Res* 22, 321-332 (2012).

10 Lujan, E., Chanda, S., Ahlenius, H., Sudhof, T. C. & Wernig, M. Direct conversion of mouse fibroblasts to self-renewing, tripotent neural precursor cells. *Proc Natl Acad Sci USA* 109, 2527-2532 (2012).

11 Ring, K. L. et al. Direct reprogramming of mouse and human fibroblasts into multipotent neural stem cells with a single factor. *Cell Stem Cell* 11, 100-109 (2012).

12 Thier, M. et al. Direct conversion of fibroblasts into stably expandable neural stem cells. *Cell Stem Cell* 10, 473-479 (2012).

13 Tian, C. et al. Direct conversion of dermal fibroblasts into neural progenitor cells by a novel cocktail of defined factors. *Curr Mol Med* 12, 126-137 (2012).

14 Li, W. et al. Rapid induction and long-term self-renewal of primitive neural precursors from human embryonic stem cells by small molecule inhibitors. *Proc Natl Acad Sci USA* 108, 8299-8304 (2011).

15 Holmin, S., Almqvist, P., Lendahl, U. & Mathiesen, T. Adult nestin-expressing subependymal cells differentiate to astrocytes in response to brain injury. *Eur J Neurosci* 9, 65-75 (1997).

16 Johansson, C. B. et al. Identification of a neural stem cell in the adult mammalian central nervous system. *Cell* 96, 25-34 (1999).

17 Han, D. W. et al. Direct reprogramming of fibroblasts into neural stem cells by defined factors. *Cell Stem Cell* 10, 465-472 (2012).

18 Lai, S. et al. Direct reprogramming of induced neural progenitors: a new promising strategy for AD treatment. *Transl Neurodegener* 4, 7 (2015).

19 Zou, Q. et al. Direct conversion of human fibroblasts into neuronal restricted progenitors. *J Biol Chem* 289, 5250-5260 (2014).

20 Ang, S. L. Transcriptional control of midbrain dopaminergic neuron development. *Development* 133, 3499-3506 (2006).

21 Ferri, A. L. et al. Foxa1 and Foxa2 regulate multiple phases of midbrain dopaminergic neuron development in a dosage-dependent manner. *Development* 134, 2761-2769 (2007).

22 Xi, J. et al. Specification of midbrain dopamine neurons from primate pluripotent stem cells. *Stem Cells* 30, 1655-1663 (2012).

23 Chung, S. et al. Wnt1-Imx1a forms a novel autoregulatory loop and controls midbrain dopaminergic differentiation synergistically with the SHH-FoxA2 pathway. *Cell Stem Cell* 5, 646-658 (2009).

24 Ono, Y. et al. Differences in neurogenic potential in floor plate cells along an anteroposterior location: midbrain dopaminergic neurons originate from mesencephalic floor plate cells. *Development* 134, 3213-3225 (2007).

25 Nakatani, T., Kumai, M., Mizuhara, E., Minaki, Y. & Ono, Y. Lmx1a and Lmx1b cooperate with Foxa2 to coordinate the specification of dopaminergic neurons and control of floor plate cell differentiation in the developing mesencephalon. *Dev Biol* 339, 101-113 (2010).

26 Lin, W. et al. Foxa1 and Foxa2 function both upstream of and cooperatively with Lmx1a and Lmx1b in a feedforward loop promoting mesodiencephalic dopaminergic neuron development. *Dev Biol* 333, 386-396 (2009).

27 Prakash, N. et al. Nkx6-1 controls the identity and fate of red nucleus and oculomotor neurons in the mouse midbrain. *Development* 136, 2545-2555 (2009).

28 Chung, S. et al. ES cell-derived renewable and functional midbrain dopaminergic progenitors. *Proc Natl Acad Sci USA* 108, 9703-9708 (2011).

29 Gaspard, N. et al. An intrinsic mechanism of corticogenesis from embryonic stem cells. *Nature* 455, 351-357 (2008).

30 Mo, Z. et al. Human cortical neurons originate from radial glia and neuron-restricted progenitors. *J Neurosci* 27, 4132-4145 (2007).

31 Friling, S. et al. Efficient production of mesencephalic dopamine neurons by Lmx1a expression in embryonic stem cells. *Proc Natl Acad Sci USA* 106, 7613-7618 (2009).

32 Cassiman, D. et al. Synaptophysin: A novel marker for human and rat hepatic stellate cells. *Am J Pathol* 155, 1831-1839 (1999).

33 Nakagawa, M., Takizawa, N., Narita, M., Ichisaka, T. & Yamanaka, S. Promotion of direct reprogramming by transformation-deficient Myc. *Proc Natl Acad Sci USA* 107, 14152-14157 (2010).

34 Kim, K. S. et al. Self-renewal induced efficiently, safely, and effective therapeutically with one regulatable gene in a human somatic progenitor cell. *Proc Natl Acad Sci USA* 108, 4876-4881 (2011).

35 Hutter-Saunders, J. A., Gendelman, H. E. & Mosley, R. L. Murine motor and behavior functional evaluations for acute 1-methyl-4-phenyl-1,2,3,6-tetrahydropyridine (MPTP) intoxication. *J Neuroimmune Pharmacol* 7, 279-288 (2012).

36 Benner, E. J. et al. Therapeutic immunization protects dopaminergic neurons in a mouse model of Parkinson's disease. Proc Natl Acad Sci USA 101, 9435-9440 (2004).

37 Lee, S. H., Lumelsky, N., Studer, L., Auerbach, J. M. & McKay, R. D. Efficient generation of midbrain and hindbrain neurons from mouse embryonic stem cells. *Nat Biotechnol* 18, 675-679 (2000).

38 Perrier, A. L. et al. Derivation of midbrain dopamine neurons from human embryonic stem cells. *Proc Natl Acad Sci USA* 101, 12543-12548 (2004).

39 Roy, N. S. et al. Functional engraftment of human ES cell-derived dopaminergic neurons enriched by coculture with telomerase-immortalized midbrain astrocytes. *Nat Med* 12, 1259-1268 (2006).

40 Hargus, G. et al. Differentiated Parkinson patient-derived induced pluripotent stem cells grow in the adult rodent brain and reduce motor asymmetry in Parkinsonian rats. *Proc Natl Acad Sci USA* 107, 15921-15926 (2010).

41 Pfisterer, U. et al. Direct conversion of human fibroblasts to dopaminergic neurons. *Proc Nati Acad Sci USA* 108, 10343-10348 (2011).

42 Yan, C. H., Levesque, M., Claxton, S., Johnson, R. L. & Ang, S. L. Lmx1a and lmx1b function cooperatively to regulate proliferation, specification, and differentiation of midbrain dopaminergic progenitors. *J Neurosci* 31, 12413-12425 (2011).

43 Miyoshi, G., Bessho, Y., Yamada, S. & Kageyama, R. Identification of a novel basic helix-loop-helix gene, Heslike, and its role in GABAergic neurogenesis. *J Neurosci* 24, 3672-3682 (2004).

44 Guimera, J., Weisenhorn, D. V. & Wurst, W. Megane/Heslike is required for normal GABAergic differentiation in the mouse superior colliculus. *Development* 133, 3847-3857 (2006).

45 Nakatani, T., Minaki, Y., Kumai, M. & Ono, Y. Helt determines GABAergic over glutamatergic neuronal fate by repressing Ngn genes in the developing mesencephalon. *Development* 134, 2783-2793 (2007).

46 Bayly, R. D., Brown, C. Y. & Agarwala, S. A novel role for FOXA2 and SHH in organizing midbrain signaling centers. *Dev Biol* 369, 32-42 (2012).

47 Wallen, A. et al. Fate of mesencephalic AHD2-expressing dopamine progenitor cells in NURR1 mutant mice. *Exp Cell Res* 253, 737-746 (1999).

48 Prakash, N. et al. A Wnt1-regulated genetic network controls the identity and fate of midbrain-dopaminergic progenitors in vivo. *Development* 133, 89-98 (2006).

49 Morita, S., Kojima, T. & Kitamura, T. Plat-E: an efficient and stable system for transient packaging of retroviruses. *Gene Ther* 7, 1063-1066 (2000).

50 Jackson-Lewis, V. & Przedborski, S. Protocol for the MPTP mouse model of Parkinson's disease. *Nat Protoc* 2, 141-151 (2007).

51 Hutter-Saunders, J. A. et al. BL-1023 improves behavior and neuronal survival in 1-methyl-4-phenyl-1,2,3,6-tetrahydropyridine-intoxicated mice. *Neuroscience* 180, 293-304 (2011).

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

What is claimed is:

1. An in vitro induced dopaminergic precursor cell (iDP), consisting essentially of ectopically expressed genes or proteins of:

(1) one or both of Bm2 and Bm4, or a variant thereof, (2) Sox2 or a variant thereof, and (3) one or both of Foxa2 and Lmx1a, or a variant thereof, wherein the iDP is transdifferentiated from a somatic cell that is not a dopaminergic precursor, the iDP expresses relative to the somatic cell high levels of neural progenitor markers Sox1, PAX6, ZBTB16, Sox3, CD133 and Nestin, high levels of ventral mesencephalon markers Aldh1A1, Corin (Lrp4), Lmx1a, Msx1, Ngn2, Otx2, Mash1, Pitx3 and Nkx6.1 and minimum levels of telencephalon related markers FoxG1, GSX2, and Nkx2.1, and the iDP is a dopaminergic neuronal lineage-restricted progenitor possessing dopaminergic neuronal-restricted differentiation potential.

2. The iDP of claim 1, consisting essentially of ectopically expressed Bm2 or a variant thereof, Sox2 or a variant thereof, and Foxa2 or a variant thereof.

3. The iDP of claim 1, wherein the ectopically expressed genes are expressed from one or more vectors carrying them, or the ectopically expressed proteins are expressed from one or more mRNA encoding them.

4. The iDP of claim 1, wherein the iDP does not differentiate into a glial cell.

5. The iDP of claim 1, wherein differentiation of the iDP is independent of morphogens selected from SHH and FGF8.

6. The iDP of claim 1, wherein the iDP is self-renewable and further comprises ectopically expressed L-Myc.

7. The iDP of claim 6, wherein the ectopically expressed L-Myc is expressed under the control of doxycycline.

8. The iDP of claim 1, wherein the somatic cell is a fibroblast.

9. The iDP of claim 8, wherein the somatic cell is present in vitro.

10. The iDP of claim 1, wherein the iDP is capable of being administrated to a patient for treating a neurodegenerative disease selected from Parkinson's disease, depression, dementia and schizophrenia.

11. A population of the iDPs of claim 1, wherein more than 80% or more than 90% of the population is capable of differentiating into dopaminergic neurons.

* * * * *